US012747478B2

(12) United States Patent
Abuelela et al.

(10) Patent No.: US 12,747,478 B2
(45) Date of Patent: Sep. 29, 2026

(54) COMPOSITIONS AND METHODS FOR CANCER DIAGNOSIS AND PROGNOSIS

(71) Applicant: King Abdullah University of Science and Technology, Thuwal (SA)

(72) Inventors: Ayman F. Abuelela, Thuwal (SA); Alyaa M. Abdel-Haleem, Thuwal (SA); Xin Gao, Thuwal (SA); Jasmeen S. Merzaban, Thuwal (SA)

(73) Assignee: King Abdullah University of Science and Technology, Thuwal (SA)

( * ) Notice: Subject to any disclaimer, the term of this patent is extended or adjusted under 35 U.S.C. 154(b) by 1024 days.

(21) Appl. No.: 17/429,279

(22) PCT Filed: Feb. 10, 2020

(86) PCT No.: PCT/IB2020/051032
§ 371 (c)(1),
(2) Date: Aug. 6, 2021

(87) PCT Pub. No.: WO2020/161686
PCT Pub. Date: Aug. 13, 2020

(65) Prior Publication Data

US 2022/0136064 A1 May 5, 2022

Related U.S. Application Data

(60) Provisional application No. 62/803,449, filed on Feb. 9, 2019.

(51) Int. Cl.
*C12Q 1/6886* (2018.01)

(52) U.S. Cl.
CPC ...... *C12Q 1/6886* (2013.01); *C12Q 2600/112* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | | |
|---|---|---|---|---|
| 3,610,795 | A | 10/1971 | Antoine | |
| 2021/0108269 | A1 * | 4/2021 | Jiang ...................... | C12Q 1/686 |

FOREIGN PATENT DOCUMENTS

| | | |
|---|---|---|
| WO | 2016059585 | 4/2016 |
| WO | 2017127803 | 7/2017 |

OTHER PUBLICATIONS

Ashkani (Scientific Reports 6:26451 May 20, 2016).*
Xu (PloS One Oct. 2010 vol. 5 Issue 10 e13696 pp. 1-8).*
Chan (G&P magazine 2006 vol0 6 No. 3 pp. 20-26).*
Coleman (Drug Discovery Today. 2003. 8: 233-235).*
Whitehead (Genome Biology 2005 vol. 6 Issue 2 Article R13).*
Amoureux, et al., "Polysialic Acid Neural Cell Adhesion Molecule (PSA-NCAM) is an adverse prognosis factor in glioblastoma, and regulates olig2 expression in glioma cell lines." BMC Cancer, 10:91, (2010).
Ashkani and Naidoo, "Glycosyltransferase Gene Expression Profiles Classify Cancer Types and Propose Prognostic Subtypes." Sci Rep., 6:26451 (2016).
Bhat, et al., "Diagnostic utility of glycosyltransferase mRNA expression in gastric cancer." Hematology/Oncology and Stem Cell Therapy, 11(3):158-168. (2018).
Bresalier, et al., "Enhanced sialylation of mucin-associated carbohydrate structures in human colon cancer metastasis." Gastroenterology, 110(5): 1354-1367, (1996).
Brockhausen, "Mucin-type O-glycans in human colon and breast cancer: glycodynamics and functions." EMBO Rep., 7(6): 599-604 (2006).
Burchell, et al., "O-linked mucin-type glycosylation in breast cancer." Biochem Soc Trans., 46(4):779-788, (2018).
Cheray, et al., "Glycosylation-related gene expression is linked to differentiation status in glioblastomas undifferentiated cells." Cancer Lett., 312(1): 24-32, (2011).
Chong, et al., "ST3GAL1-Associated Transcriptomic Program in Glioblastoma Tumor Growth, Invasion, and Prognosis." J Natl Cancer Inst., 108(2): djv326, (2016).
Dall'Olio and Trinchera, "Epigenetic Bases of Aberrant Glycosylation in Cancer." Int J Mol Sci., 18(5):998 (2017).
Drake, et al., "Altered glycosylation in prostate cancer." Adv Cancer Res., 126: 345-382 (2015).
Hanski, et al., "Fucosyltransferase III and sialyl-Le(x) expression correlate in cultured colon carcinoma cells but not in colon carcinoma tissue." Glycoconj J., 13(5): 727-733 (1996).
Hassani, et al., "Phostine PST3.1a Targets MGAT5 and Inhibits Glioblastoma-Initiating Cell Invasiveness and Proliferation." Mol Cancer Res., 15(10): 1376-1387, (2017).
Hebbar, et al., "Prognostic value of tumoral sialyltransferase expression and circulating E-selectin concentrations in node-negative breast cancer patients." Int J Biol Markers, 18(2):116-122 (2003).
Holst, et al. "Glycosylation characteristics of colorectal cancer." Adv Cancer Res., 126: 203-256 (2015).
Ito, et al., "Altered mRNA expression of specific molecular species of fucosyl- and sialyl-transferases in human colorectal cancer tissues." Int J Cancer, 71(4): 556-564 (1997).
Julien, et al., "Stable expression of sialyl-Tn antigen in T47-D cells induces a decrease of cell adhesion and an increase of cell migration." Breast Cancer Res Treat., 90(1): 77-84 (2005).
Kaneko, et al., "The expression of Gal beta 1,4GlcNAc alpha 2,6 sialyltransferase and alpha 2,6-linked sialoglycoconjugates in human brain tumors." Acta Neuropathol., 91(3): 284-292 (1996).

(Continued)

*Primary Examiner* — Amanda Haney
(74) *Attorney, Agent, or Firm* — PABST PATENT GROUP LLP

(57) ABSTRACT

Compositions and method of cancer diagnosis and prognosis are disclosed. The methods rely on the expression profile of a 55 O-glycan forming GT (OGFGT) genes in multi-dimensional space was sufficient to classify cancer types from cancer patient samples in. These OGFGT genes ae used to distinguish between normal and cancer samples and cancer subtypes promoting the huge potential of utilizing this set of genes in diagnostic applications. The expression signature of OGFGT genes can also be used to determine survival profiles in samples from GBM patient samples.

13 Claims, 11 Drawing Sheets

(56) References Cited

OTHER PUBLICATIONS

Kebir, et al., "Hybrid 11C-MET PET/MRI Combined With "Machine Learning" in Glioma Diagnosis According to the Revised Glioma WHO Classification 2016." Clin Nucl Med., 44(3):214-220, (2018).
Kojima, et al., "Inhibition of selectin-dependent tumor cell adhesion to endothelial cells and platelets by blocking O-glycosylation of these cells." Biochem Biophys Res Commun., 182(3): 1288-1295 (1992).
Kroes, et al., "Focused microarray analysis of glyco-gene expression in human glioblastomas." Journal of Neurochemistry, 103(Suppl. 1):14-25 (2007).
Kudelka, et al., "Simple sugars to complex disease—mucin-type O-glycans in cancer." Adv Cancer Res 126: 53-135 (2015).
Lemjabbar-Alaoui, et al. "Glycosylation alterations in lung and brain cancer." Adv Cancer Res., 126: 305-344 (2015).
Liu, et al., "Cell Surface-Specific N-Glycan Profiling in Breast Cancer." PLoS One, 8(8):e72704 (2013).
Magalhães, et al., "Aberrant Glycosylation in Cancer: A Novel Molecular Mechanism Controlling Metastasis." Cancer Cell, 31(6): P733-735, (2017).
Marziali, et al., "Metabolic/Proteomic Signature Defines Two Glioblastoma Subtypes With Different Clinical Outcome." Sci Rep., 6:21557, (2016).
Meany and Chan, "Aberrant glycosylation associated with enzymes as cancer biomarkers." Clin Proteomics, 8(1):7 (2011).
Miller, et al., "Isocitrate Dehydrogenase-Mutant Glioma: Evolving Clinical and Therapeutic Implications." Cancer, 123(23): 4535-4546, (2017).
Mungul, et al., "Sialylated core 1 based O-linked glycans enhance the growth rate of mammary carcinoma cells in MUC1 transgenic mice." Int J Oncol., 25(4): 937-943, (2004).
Munkley and Elliott, "Hallmarks of glycosylation in cancer." Oncotarget., 7:35478-35489 (2016).
Nagae, et al., "Structure and mechanism of cancer-associated N-acetylglucosaminyltransferase-V." Nat Commun., 9(1): 3380, (2018).
Nakamori, et al., "Increased expression of sialyl Lewisx antigen correlates with poor survival in patients with colorectal carcinoma: clinicopathological and immunohistochemical study." Cancer Res. ,53(15): 3632-3637 (1993).
Nishihara, et al., "Alpha1,3-fucosyltransferase 9 (FUT9; Fuc-TIX) preferentially fucosylates the distal GlcNAc residue of polylactosamine chain while the other four alpha1,3FUT members preferentially fucosylate the inner GlcNAc residue.", FEBS Lett., 462(3): 289-294 (1999).
Oblinger, et al., "Diagnostic and prognostic value of glycosyltransferase mRNA in glioblastoma multiforme patients." Neuropathol Appl Neurbiol., 32(4): 410-418 (2006).
Oliveira-Ferrer, et al., "Role of protein glycosylation in cancer metastasis." Semin Cancer Biol., 44:141-152 (2017).
Padhiar, et al., "Upregulated β1-6 branch N-glycan marks early gliomagenesis but exhibited biphasic expression in the progression of astrocytic glioma." Am J Cancer Res., 5(3):1101-1116, (2015).
Petretti, et al., "Altered mRNA expression of glycosyltransferases in human colorectal carcinomas and liver metastases." Gut, 46(3): 359-366 (2000).
Pinho and Reis, "Glycosylation in cancer: mechanisms and clinical implications." Nat Rev Cancer., 15:540-555 (2015).
Potapenko, et al., "Glycan gene expression signatures in normal and malignant breast tissue; possible role in diagnosis and progression." Molecular Oncology, 4(2):98-118 (2010).
Shoreibah, et al., "Isolation, characterization, and expression of a cDNA encoding N-acetylglucosaminyltransferase V." J Biol Chem. 268(21): 15381-15385, (1993).
Son, et al., "SSEA-1 Is an Enrichment Marker for Tumor-Initiating Cells in Human Glioblastoma." Cell Stem Cell, 4(5): 440-452 (2009).
Stowell, et al., "Protein glycosylation in Cancer." Annu Rev Pathol., 10: 473-510 (2015).
Taniguchi, et al., "Glycans and Cancer: Role of N-Glycans in Cancer Biomarker, Progression and Metastasis, and Therapeutics." Adv Cancer Res., 126: 11-51, (2015).
Toivonen, et al., "Fuc-TIX: a versatile alpha1,3-fucosyltransferase with a distinct acceptor- and site-specificity profile." Glycobiology, 12(6): 361-368 (2002).
Tsuiji, et al., "Aberrant O-glycosylation inhibits stable expression of dysadherin, a carcinoma-associated antigen, and facilitates cell-cell adhesion." Glycobiology, 13(5): 521-527, (2003).
Varki, "Biological roles of glycans." Glycobiology, 27(1):3-49 (2017).
Veillon, et al., "Glycosylation Changes in Brain Cancer." ACS Chem Neurosci. 9(1): 51-72, (2018).
Verhaak, et al., "Integrated genomic analysis identifies clinically relevant subtypes of glioblastoma characterized by abnormalities in PDGFRA, IDH1, EGFR, and NF1." Cancer Cell 17(1): 98-110 (2010).
Waitkus, et al., "Biological Role and Therapeutic Potential of IDH Mutations in Cancer." Cancer Cell, 34(2): 186-195, (2018).
Wang, et al., "Enabling cross-study analysis of RNA-Sequencing data." bioRxiv, 110734, (2017).
Wang, et al., "Unifying cancer and normal RNA sequencing data from different sources." Sci Data., 5:180061 (2018).
Wesseling and Capper, "Who 2016 Classification of gliomas." Neuropathol Appl Neurobiol., 44(2): 139-150, (2018).
Yamamoto, et al., "Alpha2,6-sialylation of cell-surface N-glycans inhibits glioma formation in vivo." Cancer Res., 61(18): 6822-6829 (2001).
Yamamoto, et al., "alpha2,6-Sialyltransferase gene transfection into a human glioma cell line (U373 MG) result in decreased invasivity." J Neurochem., 68(6): 2566-2576 (1997).
Yamamoto, et al., "Beta1,6-N-acetylglucosamine-bearing N-glycans in human gliomas: implications for a role in regulating invasivity." Cancer Res., 60(1): 134-142, (2000).
Yeo and Johnson, "A New Family of Power Transformations to Improve Normality or Symmetry." Biometrika, 87(4): 954-959 (2000).

* cited by examiner

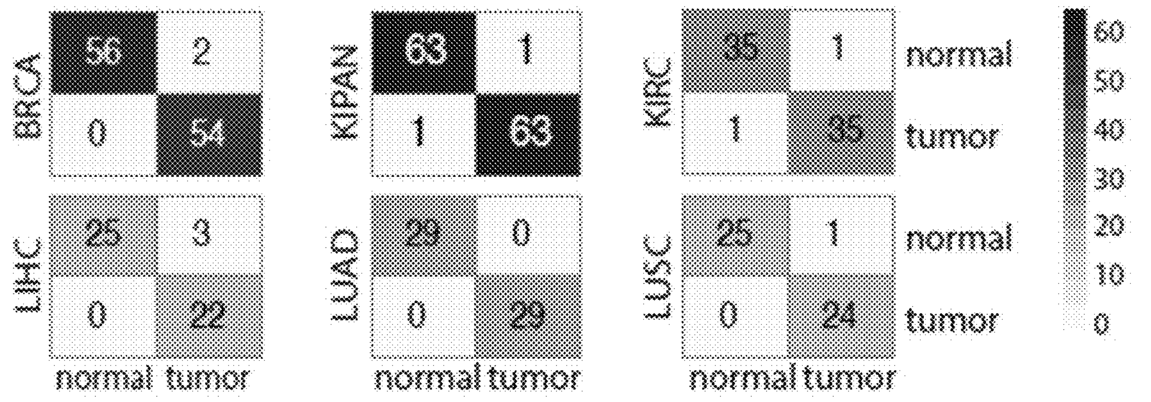
FIG. 1D
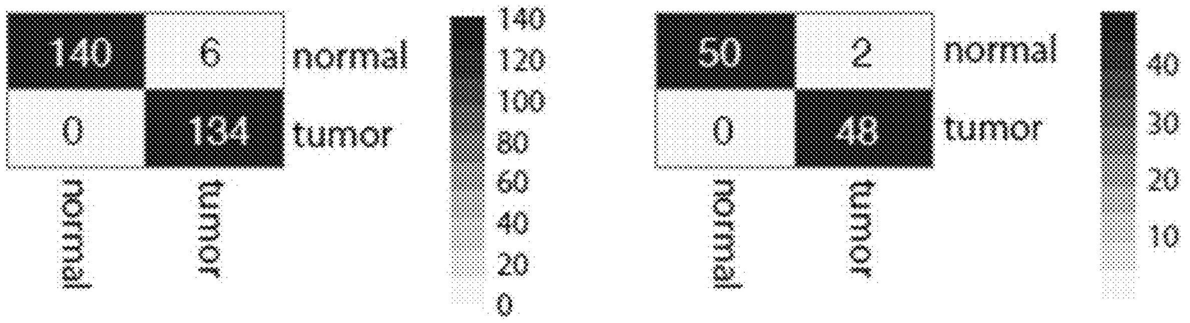
FIG. 1E
| | Sens. | Spec. | PPV | NPV | F1 |
|---|---|---|---|---|---|
| BN | 1.00 | 1.00 | 1.00 | 1.00 | 1.00 |
| KN | 1.00 | 1.00 | 0.98 | 1.00 | 0.99 |
| HN | 1.00 | 1.00 | 1.00 | 1.00 | 1.00 |
| LN | 1.00 | 1.00 | 1.00 | 1.00 | 1.00 |
| BT | 0.94 | 0.99 | 0.91 | 0.99 | 0.93 |
| KT | 0.98 | 1.00 | 1.00 | 1.00 | 0.99 |
| HT | 0.93 | 1.00 | 1.00 | 1.00 | 0.97 |
| LT | 0.94 | 0.99 | 0.94 | 0.99 | 0.94 |
FIG. 2A

| | Sens. | Spec. | PPV | NPV | F1 | BA |
|---|---|---|---|---|---|---|
| Bladder | 0.73 | 0.99 | 0.35 | 1.00 | 0.47 | 0.86 |
| Breast | 0.83 | 1.00 | 1.00 | 0.99 | 0.91 | 0.92 |
| Cervix | 0.18 | 1.00 | 0.50 | 0.99 | 0.27 | 0.59 |
| Colon | 0.79 | 1.00 | 0.99 | 0.94 | 0.88 | 0.89 |
| Kidney | 1.00 | 1.00 | 0.86 | 1.00 | 0.93 | 1.00 |
| Liver | 1.00 | 1.00 | 0.97 | 1.00 | 0.98 | 1.00 |
| Lung | 0.97 | 0.98 | 0.94 | 0.99 | 0.96 | 0.98 |
| Prostate | 0.84 | 1.00 | 1.00 | 0.99 | 0.91 | 0.92 |
| Thyroid | 1.00 | 1.00 | 0.99 | 1.00 | 1.00 | 1.00 |
| Uterus | 0.96 | 0.94 | 0.50 | 1.00 | 0.66 | 0.95 |

| | Sens | Spec | PPV | NPV | F1 | BA |
|---|---|---|---|---|---|---|
| ACC | 0.96 | 1.00 | 0.88 | 1.00 | 0.92 | 0.98 |
| BLCA | 0.76 | 1.00 | 0.94 | 0.99 | 0.84 | 0.88 |
| BRCA | 0.98 | 1.00 | 0.99 | 1.00 | 0.99 | 0.99 |
| CESC | 0.76 | 0.99 | 0.74 | 0.99 | 1.00 | 0.88 |
| COLORECTAL | 0.97 | 1.00 | 0.95 | 1.00 | 0.96 | 0.98 |
| DLBC | 1.00 | 1.00 | 0.78 | 1.00 | 0.88 | 1.00 |
| GLIOMA | 0.99 | 1.00 | 1.00 | 1.00 | 1.00 | 1.00 |
| HNSC | 0.88 | 0.98 | 0.74 | 0.99 | 0.80 | 0.93 |
| KIDNEY | 0.99 | 1.00 | 1.00 | 1.00 | 0.99 | 0.99 |
| LUNG | 0.91 | 0.99 | 0.89 | 0.99 | 0.99 | 0.95 |
| MESO | 0.88 | 1.00 | 0.96 | 1.00 | 0.92 | 0.94 |
| OV | 0.96 | 1.00 | 0.99 | 1.00 | 0.97 | 0.98 |
| PARALIVER | 0.89 | 1.00 | 1.00 | 0.99 | 0.94 | 0.95 |
| PCPG | 0.98 | 1.00 | 1.00 | 1.00 | 0.99 | 0.99 |
| PRAD | 0.99 | 1.00 | 1.00 | 1.00 | 1.00 | 1.00 |
| SARC | 0.97 | 0.99 | 0.78 | 1.00 | 0.87 | 0.98 |
| SKCM | 0.93 | 1.00 | 0.93 | 1.00 | 0.93 | 0.97 |
| STOPH | 0.82 | 1.00 | 0.91 | 0.99 | 0.86 | 0.91 |
| TGCT | 0.93 | 1.00 | 1.00 | 1.00 | 0.96 | 0.96 |
| THCA | 0.99 | 1.00 | 1.00 | 1.00 | 1.00 | 1.00 |
| THYM | 0.97 | 1.00 | 0.97 | 1.00 | 0.97 | 0.99 |
| UTERINE | 0.88 | 0.99 | 0.77 | 1.00 | 0.82 | 0.94 |
| UVM | 1.00 | 1.00 | 0.92 | 1.00 | 0.96 | 1.00 |

FIG. 3A

| | *de novo* clusters | | | | |
|---|---|---|---|---|---|
| Subtypes | 1 | 2 | 3 | 4 | 5 |
| IDHmut-codel | 3 | 1 | 0 | 164 | 1 |
| IDHmut-non-codel | 6 | 29 | 177 | 36 | 0 |
| IDHwt | 215 | 9 | 5 | 15 | 1 |

FIG. 5E

| | Sens. | Spec. | PPV | NPV | F1 | BA |
|---|---|---|---|---|---|---|
| **IDHmut-codel** | 0.987 | 0.992 | 0.977 | 0.996 | 0.982 | 0.99 |
| **IDHmut-non-codel** | 0.964 | 0.966 | 0.944 | 0.978 | 0.954 | 0.965 |
| **IDHwt** | 0.935 | 0.979 | 0.964 | 0.963 | 0.949 | 0.957 |

FIG. 6C

| | Sens. | Spec. | PPV | NPV | F1 | BA |
|---|---|---|---|---|---|---|
| **IDHmut-codel** | 0.98 | 0.973 | 0.925 | 0.993 | 0.951 | 0.976 |
| **IDHmut-non-codel** | 0.919 | 0.967 | 0.944 | 0.952 | 0.932 | 0.943 |
| **IDHwt** | 0.958 | 0.984 | 0.972 | 0.976 | 0.965 | 0.971 |

FIG. 6D

COMPOSITIONS AND METHODS FOR CANCER DIAGNOSIS AND PROGNOSIS

CROSS-REFERENCE TO RELATED APPLICATIONS

This application is a National Phase application under 35 U.S.C. § 371 of International Application No. PCT/IB2020/051032, filed on Feb. 10, 2020, which claims the benefit of U.S. Provisional Application No. 62/803,449 filed Feb. 9, 2019, which are incorporated herein by reference in their entirety.

FIELD OF THE INVENTION

The invention is generally in the field of cancer diagnosis and prognosis and in particular, relates to methods of diagnosis and prognosis of cancer based on global glycosyltransferase expression.

BACKGROUND OF THE INVENTION

Glycosylation is a post-translational modification (PTM) widely implicated in structural and functional attributes of the cell.[1] Alterations in glycan structures are fundamental to the neoplastic transformation of cancer cells.[2] Changes in glycosylation patterns are associated with invasiveness, acquisition of virulence features promoting metastasis, and epithelial-mesenchymal transition (EMT) in a wide range of solid tumors.[3] As cancer cells undergo continuous metamorphosis and microevolution, they exhibit a spectrum of heterogeneity that is reflected in their glycan profiles. Further, the developmental origin of cancer cells implies distinct glycosylation signatures across cancer types and subtypes.[4] Hence, investigation of the glycan diversity within the functional and developmental hierarchy of cancer classifications suggests a potential value for their utilization as diagnostic and/or prognostic biomarkers.

The alterations in glycan structures are the cumulative result of a collection of critical factors including the expression patterns of glycosyltransferases (GTs) and glycosidases, as well as the availability of the saccharide building blocks through transport channels or bio-synthesis pathways. Although the diversity in glycan structures is not directly encoded by the genome, the expression levels of the GTs is one of the key limiting factors in glycan biosynthesis.

Glycan modification of proteins can occur on the N-linkage of asparagine or the O-linkage of serine or threonine residues.[9] N-glycan-forming GTs have been extensively investigated previously[10,11]. However, potential roles for O-glycan forming GTs is understudied. O-glycan forming GTs, namely those involved in the formation of glycan structures such as Thomsen-nouvelle (Tn), Sialosyl-Tn antigen (STn), ThomsenFriedenreich (T), sialyltransferase (ST), core 2 and sialyl-Lewis X ($sLe^x$) are implicated in cancer formation, metastasis and invasion.[2,12-14] While the differential expression of single GTs and their use as cancer bio-markers have been sampled in a number of cancer types,[3,5-8] a pan view of the GTs as expression signatures or fingerprints of cancer heterogeneity at the different levels remains elusive.

Thus, there is a need for methods of cancer diagnosis and prognosis, which rely on O-glycan-forming glycosyltransferase expression.

It is an object of the present invention to provide methods for cancer diagnosis and prognosis using glycosyltransferase expression.

It is another object of the present invention to provide methods for cancer diagnosis and prognosis using O-glycan-forming glycosyltransferase expression.

It is a further object of the present invention to provide improved methods for cancer diagnosis and prognosis using global O-glycan-forming glycosyltransferase expression signatures.

SUMMARY OF THE INVENTION

Methods of cancer diagnosis and prognosis are provided. The methods are based on at least determining the expression profiles of O-glycan-forming glycosyltransferases (OGFGTs) from a sample in the subject. In a preferred embodiment, the OGFGTs are those involved in mucin protein-conjugated O-glycan structures, across different cancer types and levels. The disclosed OGFGTs expression profile is used to distinguish between different cancer types (for example, liver, kidney, breast, lung, etc.), cancer subtypes, as well as between the cancer and the non-cancer samples within each tissue type (i.e. matched normal/cancer samples). The data in this application revealed that the OGFGT genes exhibited distinct expression profiles across the different cancer types. Fifty-five OGFGTs are preferably used to characterize cancer at different hierarchical levels. In some preferred embodiments, OGFGT expression can be used to classify cancer subtypes in Glioblastoma multiforme (GBM).

In particular, disclosed is a method for cancer diagnosis and/or prognosis of a subject by (a) determining the expression levels of a plurality of O-glycan-forming glycosyltransferases (OGFGTs) in a sample from the subject; (b) comparing the expression level of each OGFGT in the sample to a reference level; and (c) identifying the subject as having a cancer if the expression levels of the plurality of OGFGTs corresponds to an expression signature that is indicative of having the cancer. The expression signature can be cancer type specific (e.g., the signature is sufficiently unique to one type of cancer in comparison to another to distinguish one cancer type from another, such as lung versus liver cancer).

The OGFGT expression levels in the sample can be determined to be the same, below, or above the reference levels for each respective OGFGT. The reference level can be from a normal sample (e.g., a non-cancerous sample from the same tissue type as the sample from the subject). In some embodiments, the reference levels are the expression levels in a non-cancerous sample from the subject or the expression levels in a non-cancerous sample from one or more different subjects. Preferably, the non-cancerous sample is of the same tissue type as the sample from the subject. In some embodiments, the reference levels are the expression levels in a cancerous sample from the subject or the expression levels in a cancerous sample from one or more different subjects. Preferably, the cancerous sample is of the same tissue type as the sample from the subject. The sample can include cells, tissue, or a bodily fluid. Preferably, the sample is a tissue. Determination of OGFGT expression levels can involve analysis of mRNA expression in any given sample. In some embodiments, analysis of mRNA expression is done by RNA-sequencing.

In some embodiments, expression levels of a plurality of OGFGTs selected from the following is determined: ST3GAL3, B3GNT3, C1GALT1C1, B3GNT6, CHST1, B4GALT5, B4GALT1, GALNT8, B4GALT3, GCNT7, B3GNT7, B4GALT2, FUT5, FUT4, GALNT4, ST3GAL1, ST3GAL2, FUT11, FUT2, FUT7, GALNT3, B3GNT2, GCNT2, FUT1, B4GALT4, FUT3, B3GNT5, CHST2, GALNT2, FUT9, GCNT4, B3GNT8, GALNT13, GALNT7, GALNT10, B3GNT9, GALNT6, C1GALT1, GALNT12, FUT10, B3GNT4, FUT6, B3GNT1, CHST4, ST3GAL4, GALNT5, ST3GAL6, GALNT1, GALNT9, GCNT1, GALNT14, GALNT11, ST6GALNAC1, GCNT3, and ST6GAL1. In some embodiments, the plurality of OGFGTs contains one or more glycosyltransferases involved in formation of mucin protein-conjugated O-glycan structures.

The subject can be diagnosed with any type or subtype of cancer. For example, the subject can be diagnosed as having liver cancer (e.g., hepatocellular carcinoma), kidney cancer (e.g., renal cell carcinoma), breast cancer (e.g. breast invasive carcinoma), lung cancer (e.g., lung adenocarcinoma, lung squamous cell carcinoma), and brain cancer. In particular embodiments, the subject is diagnosed with a brain cancer such as Glioblastoma multiforme (GBM). Non-limiting examples of GBM subtypes include IDH wild type GBM, IDH mutant with 1p/19q co-deletion GBM, and IDH mutant without 1p/19q co-deletion GBM.

In some embodiments, expression analysis indicates that the subject has (a) lower expression levels of a plurality of OGFGTs selected from B3GNT3, ST3GAL4, GALNT6, ST3GAL1, B3GNT2, GCNT1, CHST4, GALNT12, GALNT5, C1GALT1C1, B3GNT8, CHST2, B3GNT7, GALNT3, B3GNT9, B4GALT4, C1GALT1, GALNT7, FUT4, B4GALT1, GALNT2, B3GNT5, and GALNT4; and/or (b) higher expression levels of a plurality of OGFGTs selected from GALNT14, GALNT9, ST6GALNAC1, B3GNT1, CHST1, GALNT13, FUT9, FUT3, FUT6, and FUT5 compared to the reference levels. In such embodiments, the subject is diagnosed as having the IDH wild type subtype of GBM. In such embodiments, the subject is determined as having a negative prognosis for survival.

In some embodiments, expression analysis indicates that the subject has (a) higher expression levels of a plurality of OGFGTs selected from B3GNT3, ST3GAL4, GALNT6, ST3GAL1, B3GNT2, GCNT1, CHST4, GALNT12, GALNT5, C1GALT1C1, B3GNT8, CHST2, B3GNT7, GALNT3, B3GNT9, B4GALT4, C1GALT1, GALNT7, FUT4, B4GALT1, GALNT2, B3GNT5, and GALNT4; and/or (b) lower expression levels of a plurality of OGFGTs selected from GALNT14, GALNT9, ST6GALNAC1, B3GNT1, CHST1, GALNT13, FUT9, FUT3, FUT6, and FUT5 compared to the reference levels. In such embodiments, the subject is diagnosed as having an IDH mutant subtype of GBM. In such embodiments, the subject is determined as having a positive prognosis for survival.

In particular embodiments, expression levels of a subset of OGFGTs is sufficient to distinguish and/or diagnose one GBM subtype from another. For example, the subject can be diagnosed as having an IDH mutant with 1p/19q co-deletion GBM or IDH mutant without 1p/19q co-deletion GBM based on changes in the expression levels FUT5, GCNT2, B4GALT2, ST3GAL3, FUT4, and/or B3GNT5, when compared to a control.

The subject can undergo one or more additional diagnostic assay(s). The additional assay can be performed before, at the same time as, or after performance of the disclosed method for cancer diagnosis and/or prognosis. Exemplary assays include blood tests, mammography, non-invasive imaging, tissue biopsy, HER2 testing, and hormone status testing.

The method can additionally include providing one or more anti-cancer treatments to the subject. For example, disclosed is a method for cancer diagnosis and/or prognosis of a subject by (a) determining the expression levels of a plurality of OGFGTs in a sample from the subject; (b) comparing the expression level of each OGFGT in the sample to a reference level; (c) identifying the subject as having a cancer if the expression levels of the plurality of OGFGTs corresponds to an expression signature that is indicative of having the cancer; and (d) providing anti-cancer treatment to the subject for the cancer based upon the diagnosis and/or prognosis thereof. Exemplary anti-cancer treatments include surgery, chemotherapy, radiation therapy, immunotherapy, gene therapy, and combinations thereof. In some embodiments, chemotherapy involves administration of an effective amount of one or more chemotherapeutic agent to the subject. Exemplary chemotherapeutic agents that can be used include, without limitation, Azacitidine, Capecitabine, Carmofur, Cladribine, Clofarabine, Cytarabine, Decitabine, Floxuridine, Fludarabine, Fluorouracil, Gemcitabine, Mercaptopurine, Nelarabine, Pentostatin, Tegafur, Methotrexate, Daunorubicin, Doxorubicin, Epirubicin, Docetaxel, Paclitaxel, Vinblastine, Vincristine, and Cisplatin.

In any of the foregoing, the subject is preferably a human.

BRIEF DESCRIPTION OF THE DRAWINGS

FIGS. 1B-E. Evaluation of three normal versus cancer OGFGT-based classifiers. The normal-matched cancer RNA-Seq data from TCGA database of the four candidate cancer types was randomly split into training set (70%) and testing set (30%) except for the second type of model, the dataset was split at a 50/50 rate due to the low number of samples. The training set was normalized and used to develop a predictive model using the regularized discriminant analysis (RDA) method. The training set normalization parameters and predictive model was applied to the testing set for internal blind validation. This modeling pipeline was used to develop three different classifiers: type- and tumorgenecity classifier, tumorgenecity-in-one-type-at-a-time classifiers and tumorgenecity-in-six types classifier. (FIG. 1B) A confusion matrix of the 10-fold cross validation of the OGFGT type-and-tumorgenecity classifier. (FIG. 1C) A confusion matrix of the internal testing of the type-and-tumorgenecity classifier. (FIG. 1D) Confusion matrices of the internal testing tumorgenecity-in-one-type-at-a-time classifier. (FIG. 1E) Confusion matrices of the 10-fold cross validation (left) and the internal testing (right) of the tumorgenecity-in-six-types classifier. Predictions are in the rows and the truths are in the columns. BN, normal breast; KN, normal kidney; HN, normal liver; LN, normal lung; BT, breast tumor; KT, kidney tumor; HT, liver tumor; LT, lung tumor.

FIG. 2A Performance metrics of the OGFGT-based normal-tumor and cancer type classifier in the internal testing.

FIG. 3A. Performance metrics of the predictions of the OGFGT-based cancer type predictive model on the internal testing subset.

FIG. 5C. Kaplan-Meier survival plot of the conventional subtypes of glioblastoma according to the IDH mutation status and the 1p/19q co-deletion. FIG. 5D. Kaplan-Meier survival plots of the de novo clusters developed using the shrunken centroid algorithm on the normalized expression data of the OGFGT genes of the glioblastoma samples at the solution of k=5. (FIG. 5E.) Distribution of the OGFGT-based de novo clustered glioblastoma samples in conventional subtypes.

FIGS. 6A-6D. Confusion matrices of the model prediction over the 10-fold cross validation runs (FIG. 6A) and the internal testing subset (FIG. 6B). (FIG. 6C) Performance metrics of the 10-fold cross validation of the OGFGT-based glioblastoma subtype classifier. (FIG. 6D) Performance metrics of the testing subset of the OGFGT-based glioblastoma subtype classifier. Sens., sensitivity; Spec., specificity; PPV, positive predictive value; NPV, negative predictive value; F1, F1 score; BA, balanced accuracy.

DETAILED DESCRIPTION OF THE INVENTION

I. Definitions

Figure 1A:
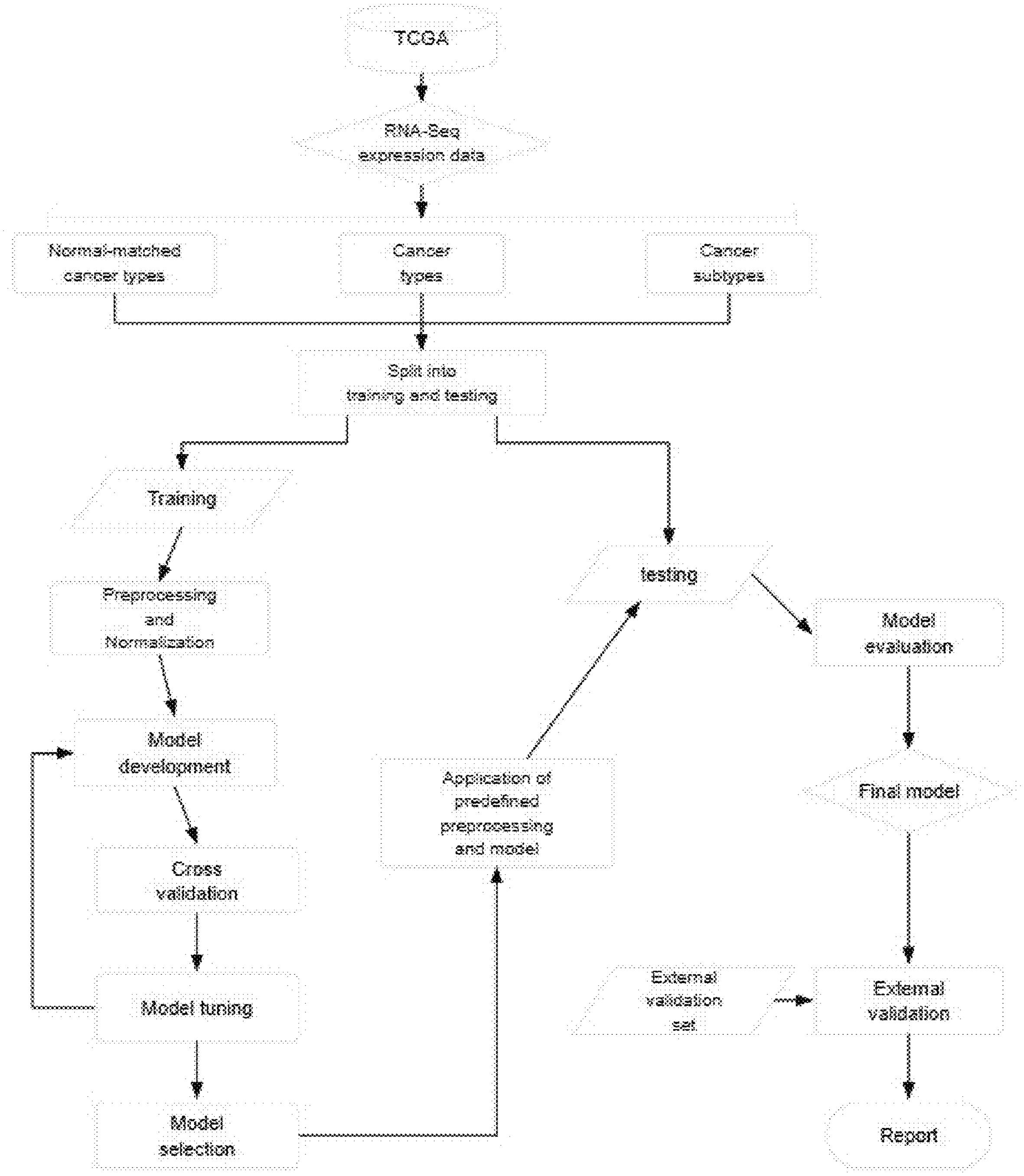
FIG. 1A shows the pipeline for the development of an OGFGT-based predictive model in a set of cancer related problems including neoplastic transformation (normal versus tumor), cancer types and cancer subtypes.

As used herein, the terms "determine", "determining", "detect", "detecting", or "measuring" are used interchangeably and generally refer to obtaining information. Detecting or determining can utilize any of a variety of techniques available to those skilled in the art, including for example specific techniques explicitly referred to herein. Detecting or determining may involve manipulation of a physical sample, consideration and/or manipulation of data or information, for example utilizing a computer or other processing unit adapted to perform a relevant analysis, and/or receiving relevant information and/or materials from a source. Detecting or determining may also mean comparing an obtained value to a known value, such as a known test value, a known control value, or a threshold value. Detecting or determining may also mean forming a conclusion based on the difference between the obtained value and the known value.

As used herein, the term "comparing" refers to making an assessment of how the proportion or expression level of one or more genes in a sample from a patient relates to the proportion or expression level of the corresponding one or more genes in a reference or standard or control sample. For example, "comparing" may refer to assessing whether the expression level of one or more genes in a sample from a patient is the same as, more than, or less than, the expression level in a reference or standard or control sample. More specifically, the term may refer to assessing whether the proportion or expression level of one or more genes in a sample from a patient is the same as, more or less than, different from or otherwise corresponds (or not) to the proportion or expression level of predefined gene levels/ratios that correspond to, for example, a patient having cancer, not having cancer, is responding to treatment for cancer, is not responding to treatment for cancer, is/is not likely to respond to a particular cancer treatment, or having/not having another disease or condition. In a specific embodiment, the term "comparing" refers to assessing whether the level of one or more disclosed OGFGTs in a sample from a patient is the same as, more or less than, different from other otherwise correspond (or not) to levels/ratios of the same OGFGTs in a control sample (e.g., predefined levels/ratios that correlate to non-diseased individuals, etc.). In the context of comparing, "higher expression" refers to the level of expression of a gene being increased in one sample relative to another sample. Conversely, "lower expression" refers to the level of expression of a gene being reduced in one sample relative to another sample. The increase or reduction can be by any amount, and can be expressed in absolute or relative (e.g., fold change) terms. The increase or reduction can be, but is not necessarily, statistically significant.

The term "expression" is used herein to mean the process by which a polypeptide is produced from DNA. The process involves the transcription of the gene into mRNA and the translation of this mRNA into a polypeptide. Depending on the context in which used, "expression" may refer to the production of RNA, protein or both.

A "reference" sample or value (also described herein as "control" sample or value) refers to a sample that serves as a reference, usually a known reference, for comparison to a test sample. For example, a test sample can be taken from a test subject, and a reference/control sample can be taken from a control subject, such as from a known normal (e.g., non-diseased) individual or a known and diagnosed individual. A reference/control can also represent a value (e.g., median, mean) gathered from a population of similar individuals, e.g., diseased patients or non-diseased or healthy individuals with a similar medical background, e.g., same age, weight, etc. A control value can also be obtained from the same individual, e.g., from an earlier-obtained sample, prior to disease, or prior to treatment, from the same tissue/organ in the subject, or from a non-diseased tissue/organ in the subject. One of skill will recognize that references or controls can be designed for assessment of any number of parameters.

As used herein, the term "sample" encompasses a variety of sample types obtained from a patient, individual, or subject. A sample may be obtained from a healthy subject, a diseased subject or a subject having symptoms associated with a disease or disorder (e.g., cancer). A sample obtained from a patient can be divided and only a portion may be used (e.g., for diagnosis). The sample, or a portion thereof, can be stored under conditions to maintain sample for later analysis. Samples can be manipulated in any way after their procurement, such as by centrifugation, filtration, precipitation, dialysis, chromatography, treatment with reagents, washed, or enriched for certain cell populations. "Sample" specifically encompasses blood and other liquid samples of biological origin, solid tissue samples such as a biopsy specimen or tissue cultures or cells derived therefrom and the progeny thereof. "Sample" includes cells, tissues, organs or portions thereof that are isolated from a subject. A sample may a plurality of cells. A sample may be a specimen obtained by biopsy (e.g., surgical biopsy). Samples can be fresh-frozen and/or formalin-fixed, paraffin-embedded tissue blocks, such as blocks prepared from clinical or pathological biopsies, prepared for pathological analysis or study by immunohistochemistry. A sample may be an intact organ or tissue. A sample may be one or more of cells or tissue.

As used herein, the terms "tissue", in a context of a sample, refers to a tissue in or from a body. The tissue may be from an organ with a pathology, for example, tissue containing tumors, whether primary or metastatic lesions. In some embodiments, an organ or tissue is normal (e.g., healthy). The term "control tissue" is used to mean an organ or tissue other than the organ or tissue of the test subject.

As used herein, the terms "subject," "individual" or "patient" refer to a human or a non-human mammal A subject may be a non-human primate, domestic animal, farm animal, or a laboratory animal. For example, the subject may be a dog, cat, goat, horse, pig, mouse, rabbit, or the like. The subject may be a human. The subject may be healthy, susceptible to, or suffering from a disease, disorder or condition. A patient refers to a subject afflicted with a disease, disorder or condition. The term "patient" includes human and veterinary subjects.

As used herein, the term "diagnosing" refers to steps taken to identify the nature of a disease or condition that a subject may be suffering from. As used herein, the term "diagnosis" refers to the determination and/or conclusion that a subject suffers from a particular disease or condition. The term "diagnosing" may denote the disease's identification (e.g., by an authorized physician or a test approved from a health care authority).

As used herein, the term "prognosis" relates to a prediction of a disease course, disease duration, and/or expected survival time. Prognosis informs of the likely outcome or course of a disease; the chance of recovery or recurrence. A complete prognosis may include the expected duration, the function, and a description of the course of the disease, such as progressive decline, intermittent crisis, or sudden, unpredictable crisis, as well as duration of the disease, or mean/median expected survival. Typically, scientifically-deduced prognosis is based on information gathered from various epidemiologic, pathologic, and/or molecular biologic studies involving subjects suffering from a disease for which a prognosis is sought. The term "prognosis" may denote the forecasting of disease evolution.

For example, prognosis may include estimating cancer-specific survival (the percentage of patients with a specific type and stage of cancer who have not died from their cancer during a certain period of time after diagnosis), relative survival (the percentage of cancer patients who have survived for a certain period of time after diagnosis compared to people who do not have cancer), overall survival (the percentage of people with a specific type and stage of cancer who have not died from any cause during a certain period of time after diagnosis), or disease-free survival (also referred to as recurrence-free or progression-free survival, this is the percentage of patients who have no signs of cancer during a certain period of time after treatment). Prognosis may also include a negative prognosis for positive outcome, or a positive prognosis for a positive outcome.

As used herein, "good prognosis" or "positive prognosis" indicates that the subject is expected (e.g. predicted) to survive and/or have no, or is at low risk of having, recurrence or distant metastases within a set time period. The term "low" is a relative term. A "low" risk can be considered as a risk lower than the average risk for a heterogeneous cancer patient population. A "low" risk of recurrence may be considered to be lower than 5%, 10%, or 15% of the average risk for a heterogeneous cancer patient population. The risk will also vary in function of the time period. The time period can be, for example, five years, ten years, fifteen years, twenty years or more after initial diagnosis of cancer or after the prognosis was made.

As used herein, "poor prognosis" or "negative prognosis" indicates that the subject is expected (e.g. predicted) to not survive and/or to have, or is at high risk of having, recurrence or distant metastases within a set time period. The term "high" is a relative term. A "high" risk can be considered as a risk higher than the average risk for a heterogeneous cancer patient population. A "high" risk of recurrence may be considered to be higher than 5%, 10%, or 15% of the average risk for a heterogeneous cancer patient population. The risk will also vary in function of the time period. The time period can be, for example, five years, ten years, fifteen years, twenty years or more after initial diagnosis of cancer or after the prognosis was made.

As used herein, the term "median survival" refers to the length of time from either the date of diagnosis or the start of treatment for a disease, such as cancer, during which half of the patients in a group of patients diagnosed with the disease are still alive.

As used herein, the term "effective amount" means a quantity sufficient to alleviate or ameliorate one or more symptoms of a disorder, disease, or condition being treated, or to otherwise provide a desired pharmacologic and/or physiologic effect. Such amelioration only requires a reduction or alteration, not necessarily elimination. The precise quantity will vary according to a variety of factors such as subject-dependent variables (e.g., age, immune system health, weight, etc.), the disease or disorder being treated, as well as the route of administration, and the pharmacokinetics and pharmacodynamics of the agent being administered. Thus, an appropriate effective amount can be determined by one of ordinary skill in the art using only routine experimentation.

"Treatment" or "treating" means to administer a composition to a subject or a system with an undesired condition (e.g., cancer). The condition can include one or more symptoms of a disease, pathological state, or disorder. Treatment includes medical management of a subject with the intent to cure, ameliorate, stabilize, or prevent a disease, pathological condition, or disorder. This includes active treatment, that is, treatment directed specifically toward the improvement of a disease, pathological state, or disorder, and also includes causal treatment, that is, treatment directed toward removal of the cause of the associated disease, pathological state, or disorder. In addition, this term includes palliative treatment, that is, treatment designed for the relief of symptoms rather than the curing of the disease, pathological state, or disorder; preventative treatment, that is, treatment directed to minimizing or partially or completely inhibiting the development of the associated disease, pathological state, or disorder; and supportive treatment, that is, treatment employed to supplement another specific therapy directed toward the improvement of the associated disease, pathological state, or disorder. It is understood that treatment, while intended to cure, ameliorate, stabilize, relieve symptoms, or prevent a disease, pathological condition, or disorder, need not actually result in the cure, amelioration, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%.

II. OGFGTs as Biomarkers of Cancer

Cancer is a leading cause of death. Thus early and accurate diagnosis of cancer is critical for effective management of this disease and for positive prognosis. Gene expression profiling, also referred to as molecular profiling, provides a powerful method for early and accurate diagnosis of tumors or other types of cancers from a biological sample.

Typically, screening for the presence of cancer involves analyzing a biological sample taken by various methods such as, for example, a biopsy. The biological sample is then prepared and examined by one skilled in the art. The methods of preparation can include but are not limited to various cytological stains, and immuno-histochemical methods. Traditional methods of cancer diagnosis suffer from a number of deficiencies, including: 1) the diagnosis may require a subjective assessment and thus be prone to inaccuracy and lack of reproducibility, 2) the methods may fail to determine the underlying genetic, metabolic or signaling pathways responsible for the resulting pathogenesis, 3) the methods may not provide a quantitative assessment of the test results, and 4) the methods may be unable to provide an unambiguous diagnosis for certain samples.

In some embodiments, the disclosed methods improve upon the accuracy of current methods of cancer diagnosis and/or prognosis. Improved accuracy can result from measuring the expression of multiple genes, the identification of particular genes whose expression yield high diagnostic power or statistical significance, or the identification of groups of genes and/or expression products with high diagnostic power or statistical significance, or any combination thereof. For example, measurement of the expression level of a particular gene known to be differentially expressed in cancer cells may provide incorrect diagnostic results leading to a low accuracy rate. Measurement of the expression level of a plurality of genes may increase accuracy by requiring a combination of multiple genes to occur. In some cases, measurement of expression of a plurality of genes might therefore increase the accuracy of a diagnosis by reducing the likelihood that a sample may exhibit a particular gene expression profile by random chance. In the context of genes such as OGFGTs, plurality encompasses any number or range of numbers that is more than 1 (e.g., 2 or more, 2-55). Thus a plurality of OGFGTs can be 2 or more OGFGTs (e.g., 55).

It has been discovered that the combined expression patterns of a set of OGFGTs whose expression is changed or unchanged in a sample as compared to a reference sample may be indicative of cancer. Furthermore, the particular expression profile of the set of OGFGTs may be indicative of a particular type or subtype of cancer. The compositions and methods disclosed herein are based on an analysis of the expression profiles of the O-glycan type GTs to study the relative distribution of cancer hierarchies over the information space of the O-glycan-forming glycosyltransferases (OGFGTs). A comprehensive analysis of the expression profiles of the OGFGT genes was carried out to discover the relative contribution of OGFGTs in characterizing cancer from non-cancer cells, and distinguishing between cancer types as well as cancer subtypes. These studies revealed that OGFGTs are discriminating features across the different hierarchies of tumorigenesis.

Methods of cancer diagnosis and prognosis are provided. The methods are based on determining the expression profiles of O-glycan-forming glycosyltransferases (OGFGTs) from a sample in the subject. For example, disclosed is a method for cancer diagnosis and/or prognosis of a subject including the step of determining the expression levels of a plurality of O-glycan-forming glycosyltransferases (OGFGTs) in a sample from the subject.

The plurality of OGFGTs can be any set of two or more OGFGTs. Thus, in some embodiments, the disclosed methods measure expression levels of two or more (e.g., 5-55) OGFGTs. For example, in some embodiments, the expression levels of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 OGFGTs is determined (e.g., from a group of OGFGTs). In some embodiments, the expression levels of about 5, about 10, about 15, about 20, about 25, about 30, about 35, about 40, about 45, about 50, or about 55 OGFGTs is determined.

Non-limiting examples of OGFGTs that can be used in accordance with the disclosed methods are provided in Table 1.

TABLE 1

| Exemplary OGFGTs | | | | |
|---|---|---|---|---|
| ST3GAL3 | B3GNT3 | C1GALT1C1 | B3GNT6 | CHST1 |
| B4GALT5 | B4GALT1 | GALNT8 | B4GALT3 | GCNT7 |
| B3GNT7 | B4GALT2 | FUT5 | FUT4 | GALNT4 |
| ST3GAL1 | ST3GAL2 | FUT11 | FUT2 | FUT7 |
| GALNT3 | B3GNT2 | GCNT2 | FUT1 | B4GALT4 |
| FUT3 | B3GNT5 | CHST2 | GALNT2 | FUT9 |
| GCNT4 | B3GNT8 | GALNT13 | GALNT7 | GALNT10 |
| B3GNT9 | GALNT6 | C1GALT1 | GALNT12 | FUT10 |
| B3GNT4 | FUT6 | B3GNT1 | CHST4 | ST3GAL4 |
| GALNT5 | ST3GAL6 | GALNT1 | GALNT9 | GCNT1 |
| GALNT14 | GALNT11 | ST6GALNAC1 | GCNT3 | ST6GAL1 |

In some embodiments, the 55 OGFGTs listed in Table 1 are preferably used to characterize (e.g., diagnose and/or prognosticate) cancer at different hierarchical levels. In some embodiments, less than 55 OGFGTs can also be used. For example, in some embodiments, about 2-10, about 5-15, about 10-20, about 15-25, about 20-30, about 25-35, about 30-40, about 35-45, about 40-50, or about 45-55 of any of the OGFGTs listed in Table 1 can be used.

In some embodiments, a plurality of OGFGTs is selected from a list of OGFGTs including B3GNT3, ST3GAL4, GALNT6, ST3GAL1, B3GNT2, GCNT1, CHST4, GALNT12, GALNT5, C1GALT1C1, B3GNT8, CHST2, B3GNT7, GALNT3, B3GNT9, B4GALT4, C1GALT1, GALNT7, FUT4, B4GALT1, GALNT2, B3GNT5, and GALNT4. This subset of OGFGTs tend towards lower expression in IDH wild type GBM but higher expression in IDH mutant GBM. In some embodiments, a plurality of OGFGTs is selected from a list of OGFGTs including GALNT14, GALNT9, ST6GALNAC1, B3GNT1, CHST1, GALNT13, FUT9, FUT3, FUT6, and FUT5. This subset of OGFGTs tend towards lower expression in IDH mutant GBM but higher expression in IDH wild type GBM. In some embodiments, the expression level of one or more glycosyltransferases involved in formation of mucin protein-conjugated O-glycan structures is determined. Mucins are heavily O-glycosylated glycoproteins found in mucous secretions and as transmembrane glycoproteins of the cell surface with the glycan exposed to the external environment. The mucins in mucous secretions can be large and polymeric (gel-forming mucins) or smaller and monomeric (soluble mucins). In mucins, O-glycans are covalently α-linked via an N-acetylgalactosamine (GalNAc) moiety to the —OH of serine or threonine by an O-glycosidic bond, and the structures are named mucin O-glycans or O-GalNAc glycans. The simplest mucin O-glycan is a single N-acetylgalactosamine residue linked to serine or threonine. Named the Tn antigen, this glycan is often antigenic. The most common O-GalNAc glycan is Galβ1-3GalNAc—, and it is found in many glycoproteins and mucins. Exemplary glycosyltransferases that are involved in the assembly of mucin O-GalNAc glycans include, Polypeptide N-acetylgalactosaminyltransferase (ppGalNAcT-1 to -24), Core 1 β1-3 galactosyltransferase (C1GalT-1 or T synthase), Core 2 β1-6 N-acetylglucosaminyltransferase (C2GnT-1, C2GnT-3), Core 3 β1-3 N-acetylglucosaminyltransferase (C3GnT-1), Core 2/4 β1-6 N-acetylglucosaminyltransferase (C2GnT-2), Elongation β1-3 N-acetylglucosaminyltransferase (elongation β3GnT-1 to -8), Core 1 α2-3 sialyltransferase (ST3Gal I, ST3Gal IV), α2-6 sialyltransferase (ST6GalNAc I, II, III or IV), Core 1 3-O-sulfotransferase (Gal3ST4), and Secretor gene α1-2 fucosyltransferase (FucT-I, FucT-II). See also Brockhausen I, Stanley P, Essentials of Glycobiology [Internet]. 3rd edition. Cold Spring Harbor (NY): Cold Spring Harbor Laboratory Press; 2015-2017. Chapter 10. 2017.).

A. Determining Expression Levels

The disclosed methods include determining the expression levels of genes of interest (e.g., O-glycan-forming glycosyltransferases) in a sample. Various assays known in the art can be used to measure genes at the DNA, mRNA, or protein levels. Thus, OGFGTs can be measured at the mRNA level.

In preferred embodiments, determining the expression levels of genes of interest such as OGFGTs is performed at the mRNA level. Methods of gene expression profiling directed to the measurement of mRNA levels can be divided into two large groups: methods based on polynucleotide hybridization analysis, and methods based on polynucleotide sequencing. These include Northern blotting and in situ hybridization (Parker & Barnes, Methods in Molecular Biology 106: 247-283 (1999)); RNAse protection assay (Hod, Biotechniques 13: 852-854 (1992)); and reverse transcription polymerase chain reaction (RT-PCR) (Weis et al., Trends in Genetics 8: 263-264 (1992)). Alternatively, antibodies that can recognize specific duplexes, including DNA duplexes, RNA duplexes, and DNA-RNA hybrid duplexes or DNA-protein duplexes, can be used. Representative methods for gene expression analysis based on sequencing include gene expression analysis by continuous gene expression analysis (SAGE), massively parallel gene bead clone analysis (MPSS) and next-generation RNA sequencing (e.g., deep sequencing, whole transcriptome sequencing, exome sequencing).

The expression levels of genes of interest are determined using methods known in the art, for example RT-qPCR. In this technique, reverse transcription is followed by quantitative PCR. Reverse transcription first generates a DNA template from the mRNA; this single-stranded template is called cDNA. The cDNA template is then amplified in the quantitative step, during which the fluorescence emitted by labeled hybridization probes or intercalating dyes changes as the DNA amplification process progresses. With a carefully constructed standard curve, qPCR can produce an absolute measurement of the number of copies of original mRNA, typically in units of copies per nanolitre of homogenized tissue or copies per cell. qPCR is very sensitive (detection of a single mRNA molecule is theoretically possible), but can be expensive depending on the type of reporter used; fluorescently labeled oligonucleotide probes are more expensive than non-specific intercalating fluorescent dyes.

For expression profiling, or high-throughput analysis of many genes within a sample, quantitative PCR may be performed for hundreds of genes simultaneously in the case of low-density arrays. A second approach is the hybridization microarray. A single array or "chip" may contain probes to determine transcript levels for every known gene in the genome of one or more organisms. Alternatively, "tag based" technologies like Serial analysis of gene expression (SAGE) and RNA-Seq, which can provide a relative measure of the cellular concentration of different mRNAs, can be used. In preferred embodiments, RNA sequencing can be performed. Typically, total RNA is extracted from a sample e.g., using Trizol (Thermo Fisher) or RNAeasy kit (Qiagen). The RNA can then be DNase treated and used as input for library preparation with poly(A) selection (e.g., using Illumina's TruSeq Stranded mRNA Library Preparation Kit and protocol). Libraries can then be sequenced using an appropriate platform (e.g., NextSeq 500 machine). Sequenced reads are aligned to the human genome assembly. Transcript levels are quantified and normalized by various methods known in the art, e.g., by calculating the RPKM (reads per kilobase of transcript per million mapped reads), FPKM (fragments per kilobase of transcript per million mapped reads), or TPM[54] (transcripts per kilobase million) values. In specific embodiments, normalization of RNA-SEQ data is performed as described in Wang et al. (Reference 54; Pubmed ID: 29664468).

In some embodiments, the expression of one or more normalizing genes is also determined for use in normalizing the expression of test genes (e.g., OGFGTs). As used herein, "normalizing genes" refers to the genes whose expression is used to calibrate or normalize the measured expression of the gene of interest (e.g., test genes).

The expression of normalizing genes should be independent of physiological state, cancer outcome and/or prognosis. For example, the expression of the normalizing genes is very similar among all the tissue types or samples. The normalization ensures accurate comparison of expression of a test gene between different samples. For this purpose, housekeeping genes known in the art can be used. Housekeeping genes are typically constitutive genes that are required for the maintenance of basal cellular functions that are essential for the existence of a cell, regardless of its specific role in the tissue or organism. Thus, they are expressed in all cells of an organism under normal and patho-physiological conditions, irrespective of tissue type, developmental stage, cell cycle state, or external signal. Housekeeping genes are well known in the art. Exemplary housekeeping genes that can be used include, but are not limited to, 18S ribosomal RNA (RRN18S), beta-Actin (ACTB), Glyceraldehyde-3-phosphate dehydrogenase (GAPDH), Phosphoglycerate kinase 1 (PGK1), Peptidylprolyl isomerase A (PPIA), Ribosomal protein L13a (RPL13A), Beta-2-microglobulin (B2M), GUSB (glucuronidase, beta), HMBS (hydroxymethylbilane synthase), SDHA (succinate dehydrogenase complex, subunit A, flavoprotein), UBC (ubiquitin C), and YWHAZ (tyrosine 3-monooxygenase/tryptophan 5-monooxygenase activation protein, zeta polypeptide). One or more housekeeping genes can be used.

B. OGFGT Expression Signatures

The disclosed methods can also include determining whether the OGFGT expression levels in a subject (e.g., patient) correspond to a specific gene expression signature or profile (e.g., a cancer gene expression signature or profile) . For example, in some embodiments, disclosed are methods for cancer diagnosis and/or prognosis of a subject including the steps of (a) determining the expression levels of a plurality of O-glycan-forming glycosyltransferases (OGFGTs) in a sample from the subject, (b) comparing the expression level of each OGFGT in the sample to a reference level; and (c) identifying the subject as having a cancer if the expression levels of the plurality of OGFGTs corresponds (e.g., correlates) to an expression signature that indicates the presence of the cancer.

An expression signature or profile refers to the combined set of levels and patterns of expression of a plurality of genes (e.g., OGFGTs) in a particular physiological state, tissue, disease, condition, etc. Within a signature, each gene may exhibit an independent level and direction of change relative to a reference or standard. It is the combination of these unique patterns that constitute the expression signature or profile for the genes contained in the set. For example, genes can exhibit qualitative or quantitative differences in the changes of expression. In some embodiments, the difference in gene expression level between a test sample and a reference sample that can be used to identify, classify, diagnose or prognosticate cancer is at least 1.5, 2, 2.5, 3, 3.5, 4, 4.5, 5, 5.5, 6, 6.5, 7, 7.5, 8, 8.5, 9, 9.5, 10 fold or more. Such fold changes in expression can be in any direction (e.g., up or down) in relation to the reference. The changes can be, but need not be, statistically significant. By “statistically significant”, it is meant that the result is observed or achieved greater than what might be expected to happen by chance alone. Statistical significance can be determined by any method known in the art. Commonly used measures of significance include the p-value, which presents the probability of obtaining a result at least as extreme as a given data point, assuming the data point was the result of chance alone. A result is often considered highly significant at a p-value of 0.05 or less and statistically significant at a p-value of 0.10 or less. Such p-values depend significantly on the power of the study performed. As shown in the Examples, rigorous statistical and machine learning models can be used with standard evaluation metrics for assessing the model’s performance.

The expression profile can be unique, e.g., to a particular physiological state, tissue, disease, condition, etc. and may thus constitute a “signature” for that particular physiological state, tissue, disease, condition, etc. For example, an expression signature can be cancer type specific (e.g., the signature is sufficiently unique to one type of cancer in comparison to another to distinguish one cancer type from another, such as lung versus liver cancer). An expression signature can be cancer subtype specific (e.g., the signature is sufficiently unique to one subtype of cancer in comparison to another to distinguish one subtype from another, such as the IDH wild type and IDH mutant GBM subtypes). An expression signature can also be specific to a normal (e.g., non-cancerous) state. One of skill in the art can appreciate that the same set of genes can be used to classify, identify, diagnose, or prognosticate different types of cancer. This is at least because the changes in expression across the gene set being used (in relation to a reference) can be specific to one type of cancer as compared to another.

Thus in some embodiments, the determination of the expression levels of an identical plurality (e.g., 55) of OGFGTs selected from ST3GAL3, B3GNT3, C1GALT1C1, B3GNT6, CHST1, B4GALT5, B4GALT1, GALNT8, B4GALT3, GCNT7, B3GNT7, B4GALT2, FUT5, FUT4, GALNT4, ST3GAL1, ST3GAL2, FUT11, FUT2, FUT7, GALNT3, B3GNT2, GCNT2, FUT1, B4GALT4, FUT3, B3GNT5, CHST2, GALNT2, FUT9, GCNT4, B3GNT8, GALNT13, GALNT7, GALNT10, B3GNT9, GALNT6, C1GALT1, GALNT12, FUT10, B3GNT4, FUT6, B3GNT1, CHST4, ST3GAL4, GALNT5, ST3GAL6, GALNT1, GALNT9, GCNT1, GALNT14, GALNT11, ST6GALNAC1, GCNT3, and ST6GAL1 is used for diagnosis and/or prognosis of cancer, such as liver, kidney, breast, lung, or brain cancer. Preferably, the determination of the expression levels of all of the following OGFGTs is used for diagnosis and/or prognosis of cancer, such as liver, kidney, breast, lung, or brain cancer: ST3GAL3, B3GNT3, C1GALT1C1, B3GNT6, CHST1, B4GALT5, B4GALT1, GALNT8, B4GALT3, GCNT7, B3GNT7, B4GALT2, FUT5, FUT4, GALNT4, ST3GAL1, ST3GAL2, FUT11, FUT2, FUT7, GALNT3, B3GNT2, GCNT2, FUT1, B4GALT4, FUT3, B3GNT5, CHST2, GALNT2, FUT9, GCNT4, B3GNT8, GALNT13, GALNT7, GALNT10, B3GNT9, GALNT6, C1GALT1, GALNT12, FUT10, B3GNT4, FUT6, B3GNT1, CHST4, ST3GAL4, GALNT5, ST3GAL6, GALNT1, GALNT9, GCNT1, GALNT14, GALNT11, ST6GALNAC1, GCNT3, and ST6GAL1.

In some embodiments, the determination of the expression levels of an identical plurality of OGFGTs selected from B3GNT3, ST3GAL4, GALNT6, ST3GAL1, B3GNT2, GCNT1, CHST4, GALNT12, GALNT5, C1GALT1C1, B3GNT8, CHST2, B3GNT7, GALNT3, B3GNT9, B4GALT4, C1GALT1, GALNT7, FUT4, B4GALT1, GALNT2, B3GNT5, and GALNT4 is used for diagnosis and/or prognosis of cancer, such as liver, kidney, breast, lung, or brain cancer. In some embodiments, the determination of the expression levels of an identical plurality of OGFGTs selected from GALNT14, GALNT9, ST6GALNAC1, B3GNT1, CHST1, GALNT13, FUT9, FUT3, FUT6, and FUT5 is used for diagnosis and/or prognosis of cancer, such as liver, kidney, breast, lung, or brain cancer.

The disclosed OGFGTs expression profiles are used to distinguish between different cancer types (for example, liver, kidney, breast, lung, etc.), cancer subtypes, as well as between the cancer and the non-cancer samples within each tissue type. Exemplary cancers that can be diagnosed using the expression levels of a combination of OGFGTs are shown in FIG. 3E. Exemplary cancers that can be diagnosed using the expression levels of a combination of OGFGTs include, but are not limited to, Adrenocortical carcinoma, Bladder Urothelial Carcinoma, Breast invasive carcinoma, cervical squamous cell carcinoma and endocervical adenocarcinoma, Lymphoid Neoplasm Diffuse Large B-cell Lymphoma, glioma, Head and Neck squamous cell carcinoma, kidney cancer (e.g., Kidney Chromophobe, Kidney renal clear cell carcinoma, Kidney renal papillary cell carcinoma), lung cancer (e.g., Lung adenocarcinoma, Lung squamous cell carcinoma), Colorectal carcinoma, Mesothelioma, Ovarian serous cystadenocarcinoma, Liver hepatocellular carcinoma, Pheochromocytoma and Paraganglioma, Prostate adenocarcinoma, Sarcoma, Skin Cutaneous Melanoma, Testicular Germ Cell Tumors, Thymoma, Thyroid carcinoma, Uterine Carcinosarcoma, Uterine Corpus Endometrial Carcinoma, Uveal Melanoma.

The data in this application revealed that the OGFGT genes exhibited distinct expression profiles across the different cancer types. As demonstrated in the Examples, the collective gene expression behavior of the particular set of 55 OGFGTs listed in Table 1 can be used to broadly identify whether a sample (e.g., liver, kidney, lung, or breast) is cancerous, and thereby diagnose and/or prognosticate a subject. Thus, the gene signature or pattern is rather predictive. The model used in the Examples learns the pattern of gene expression where some genes are upregulated while others are down regulated (relative to the normal). Thus, in some embodiments, the methods can distinguish any of the following types of cancer from any other type in the list: liver cancer, breast cancer, lung cancer, kidney cancer, and brain cancer. In some preferred embodiments, OGFGT expression can be used to classify cancer subtypes in Glioblastoma multiforme (GBM), such as the IDH wild type and IDH mutant subtypes.

In some embodiments of the disclosed methods, the expression level of each OGFGT in a sample from a subject is compared to a reference level and the subject is identified as having a cancer if the expression levels of the plurality of OGFGTs corresponds (e.g., correlates) to an expression signature that indicates the presence of the cancer. OGFGT expression signatures that indicate the presence of a specific cancer (when compared to normal samples for example) have been discovered and are described below.

In some embodiments, breast cancer is diagnosed by upregulation of GALNT5, B3GNT4, B4GALT1, GALNT7, GALNT6, ST3GAL1, FUT7, ST3GAL4, B4GALT4, CHST1, B4GALT3, FUT3, GALNT4, B3GNT9, FUT2, B4GALT2, C1GALT1C2, GALNT1, and GALNT10 compared to normal (e.g., non-cancerous sample) reference levels and downregulation of FUT6, GCNT2, C1GALT1, B4GALT5, GALNT13, FUT1, ST3GAL2, GCNT7, B3GNT3, ST3GAL3, GCNT4, ST6GALNAC1, CHST2, FUT4, B3GNT5, FUT10, ST3GAL6, B3GNT1, GALNT12, CHST4, GALNT11, and GALNT8 compared to normal (e.g., non-cancerous sample from the same tissue type) reference levels. The upregulation or downregulation can be by any amount (e.g., 0.5 to 3 fold).

In some embodiments, kidney cancer is diagnosed by upregulation of FUT11, ST3GAL2, FUT7, B3GNT5, GALNT1, B4GALT5, GALNT2, GCNT1, GCNT7, GALNT5, B3GNT9, ST3GAL1, and GCNT1 compared to normal (e.g., non-cancerous) reference levels and downregulation of C1GALT1C1, B4GALT1, B3GNT7, B3GNT8, FUT6, FUT1, B3GNT3, GALNT3, ST6GAL1, GCNT4, GALNT6, FUT10, ST3GAL4, B3GNT2, ST3GAL6, GCNT2, FUT2, GALNT13, FUT3, and FUT9 compared to normal (e.g., non-cancerous) reference levels. The upregulation or downregulation can be by any amount (e.g., 0.5 to 3 fold).

In some embodiments, kidney cancer (e.g., clear cell renal cell carcinoma) is diagnosed by upregulation of GALNT2, CHST2, GALNT12, B3GNT1, B3GNT9, FUT4, B3GNT4, FUT7, B4GALT5, B3GNT5, GALNT1, ST3GAL2, GALNT14, and FUT11 compared to normal (e.g., non-cancerous) reference levels and downregulation of GALNT3, ST6GAL1, ST3GAL6, FUT10, B3GNT8, FUT2, GCNT4, GALNT6, ST3GAL4, FUT9, B3GNT2, B3GNT7, GCNT2, FUT3, B4GALT1, GALNT13, and FUT1 compared to normal (e.g., non-cancerous) reference levels. The upregulation or downregulation can be by any amount (e.g., 0.5 to 3 fold).

In some embodiments, liver cancer (e.g., hepatocellular carcinoma) is diagnosed by upregulation of B3GNT5, GCNT3, GALNT11, B3GNT4, FUT1, FUT2, GALNT10, B4GALT3, ST3GAL2, CHST1, and B3GNT1 compared to normal (e.g., non-cancerous) reference levels and downregulation of GCNT2, B3GNT2, GALNT4, FUT10, B3GNT7, B4GALT1, ST3GAL6, CHST4, ST6GALNAC1, GCNT1, FUT7, GALNT3, GALNT14, and FUT3 compared to normal (e.g., non-cancerous) reference levels. The upregulation or downregulation can be by any amount (e.g., 0.5 to 3 fold).

In some embodiments, lung cancer (e.g., lung adenocarcinoma) is diagnosed by upregulation of GALNT10, C1GALT1, B4GALT1, FUT5, GALNT1, FUT9, GALNT6, C1GALT1C1, B3GNT4, B3GNT6, FUT3, GALNT2, GCNT3, B4GALT4, GALNT14, B3GNT3, FUT2, B4GALT2, GALNT7, B4GALT3, GALNT4, B4GALT5, FUT4, GALNT3, and CHST4 compared to normal (e.g., non-cancerous) reference levels and downregulation of ST3GAL3, GALNT8, B3GNT2, B3GNT1, FUT1, ST3GAL6, GALNT13, GCNT4, B3GNT8, ST3GAL2, GALNT5, B3GNT7, GCNT7, ST3GAL1, and GCNT2 compared to normal (e.g., non-cancerous) reference levels. The upregulation or downregulation can be by any amount (e.g., 0.5 to 3 fold).

In some embodiments, lung cancer (e.g., lung squamous cell carcinoma) is diagnosed by upregulation of FUT5, C1GALT1, GALNT6, FUT9, GALNT1, GALNT3, B3GNT3, GALNT2, B3GNT5, GALNT7, B4GALT3, GALNT14, B4GALT4, B4GALT2, B3GNT4, and CHST2 compared to normal (e.g., non-cancerous) reference levels and downregulation of FUT11, ST3GAL3, B3GNT7, B3GNT8, ST3GAL6, GALNT12, GALNT5, B3GNT1, ST3GAL2, GCNT4, ST6GAL1, FUT7, GALNT10, ST3GAL1, GALNT13, GCNT2, and C1GALT1C1 compared to normal (e.g., non-cancerous) reference levels. The upregulation or downregulation can be by any amount (e.g., 0.5 to 3 fold).

In any of the foregoing embodiments, the collective expression patterns of upregulation and downregulation in the indicated OGFGTs correspond to expression signatures that indicate the presence of the cancer. These signatures are useful in the disclosed methods.

In some embodiments, the OGFGT expression signature used in accordance with the disclosed methods is based on or derived from data which shows the pattern of relative expression for each OGFGT across various cancers. For example, if the OGFGT expression pattern in a sample from a subject, is identical or similar to an expression pattern for a cancer disclosed herein, then this would indicate that the sample is or contains that cancer type. In some embodiments, uterine cancer is diagnosed by upregulation (e.g., 1-3 fold) of B4GALT1, CHST4, FUT5, GCNT1, ST6GALNAC1, B4GALT3, and B4GALT2 and downregulation (e.g., 1-3 fold) of GCNT4, GALNT5, B3GCNT6, and GCNT7, compared to the expression levels in non cancerous uterine tissue.

In some embodiments, ovarian cancer (e.g., ovarian serous cystadenocarcinoma) is diagnosed by upregulation (e.g., 1-3 fold) of B4GALT5, CHST4, FUT5, B3GNT3, GALNT3, ST6GALNAC1, GCNT7, FUT11, B3GNT2, GALNT6, B3GNT7, ST6GAL1, B4GALT2, ST3GAL6, and CHST1 and downregulation (e.g., 1-3 fold) of GCNT4, GALNT1, B3GNT5, FUT6, B3GNT6, FUT11. In some embodiments, breast cancer is diagnosed by upregulation (e.g., 1-3 fold) of B4GALT1, GALNT1, GALNT10, GALNT7, B3GNT2, GALNT6, B4GALT3, and ST3GAL1, and downregulation (e.g., 1-3 fold) of B4GALT5, C1GALT1, GALNT12, B3GNT5, GCNT3, ST6GALNAC1, B3GNT6, B3GNT4, ST3GALT2, CHST2, B3GNT1, ST3GAL3, and GALNT9.

In some embodiments, thyroid cancer is diagnosed by upregulation (e.g., 1-3 fold) of GALNT7, GCNT1, GALNT12, GALNT3, B3GNT4, GALNT14, B3GNT7, GCNT2, FUT4, GALNT8, CHST2, ST3GAL1, GALNT9, B3GALNT9, and CHST1 and downregulation (e.g., 1-3 fold) of GALNT1, B4GALNT5, C1GALT1, FUT5, FUT6, ST6GALNAC1, GALNT6, ST3GAL2, B4GALT2, ST3GAL4, and GALNT13. In some embodiments, head and neck squamous cell carcinoma is diagnosed by upregulation (e.g., 1-3 fold) of B4GALNT1, GALNT1, GALNT2, B3GNT5, FUT3, GALNT3, B3GNT8, FUT1, FUT2, B3GNT4, GALNT6, CHST2, FUT7, B4GALT2, and downregulation (e.g., 1-3 fold) of C1GALT1C1, GCNT6, ST6GAL1, GALNT8, ST3GALT2, B3GNT1, GALNT11, FUT9, and GALNT9. In some embodiments, cervical squamous cell carcinoma and endocervical adenocarcinoma (CESC) is diagnosed by upregulation (e.g., 1-3 fold) of FUT7, B3GNT4, FUT2, B3GNT8, ST6GALNAC1, GALNT3, FUT3, FUT6, B3GNT5, GALNT2, B4GALT4, and, B4GALT1, and downregulation (e.g., 1-3 fold) of CHST1, GALNT13, FUT9, GALNT11, ST3GAL3, B3GNT1, ST3GAL2, GALNT8, FUT10, and GALNT10.

In some embodiments, lung cancer is diagnosed by upregulation (e.g., 1-3 fold) of GCNT2, B4GALT3, B3GNT7, GALNT6, B3GNT2, B3GNT6, FUT1, FUT2, B3GNT8, ST6GALNAC1, GALNT3, FUT3, FUT6, B3GNT5, GALNT2, CHST4, GALNT1, B4GALT4, and B4GALT1, and downregulation (e.g., 1-3 fold) of GALNT9, and B3GNT1. In some embodiments, bladder cancer is diagnosed by upregulation (e.g., 1-3 fold) of FUT9, ST3GAL4, B4GAL2, B4GALT3, FUT3, B3GNT3, B3GNT5, GALNT1, B4GALT4 and GCNT4, and downregulation (e.g., 1-3 fold) of CHST1, GALNT9, ST3GAL6, ST3GAL3, B3GNT1, GALNT8, FUT10, ST6GAL1, GCNT2, GCNT1, and FUT5.

In some embodiments, prostate cancer is diagnosed by upregulation (e.g., 1-3 fold) of GALNT11, ST3GAL3, ST6GAL1, GCNT2, B4GALT3, B3GNT6, FUT1, ST6GALNAC1, GALNT3, GCNT1, GALNT7, and GCNT4, and downregulation (e.g., 1-3 fold) of CHST1, B3GNT9, ST3GAL1, FUT7, ST3GAL2, GALNT8, FUT10, B3GNT7, GALNT6, B3GNT2, GALNT14, FUT11, B3GNT4, FUT3, FUT6, GALNT2, CHST4, C1GALTT1, and B4GALT5. In some embodiments, sarcoma is diagnosed by upregulation (e.g., 1-3 fold) of B3GNT9, GALNT13, ST3GAL3, ST3GALT4, B4GALT2, ST3GAL2, and downregulation (e.g., 1-3 fold) of ST6GAL1, GCNT2, GALNT6, GALNT14, B3GNT4, B3GNT6, FUT2, FUT1, ST6GALNAC1, GALNT3, FUT3, B3GNT3, FUT6, GCNT3, GALNT4, GALNT7, and CHST4.

In some embodiments, adrenocortical carcinoma is diagnosed by upregulation (e.g., 1-3 fold) of B3GNT9, ST3GAL3, ST3GAL4, ST3GAL1, ST3GAL2, GALNT2, CHST4, B4GALT5 and downregulation (e.g., 1-3 fold) of FUT9, B4GAL2, CHST2, FUT4, ST6GAL1, GCNT2, B4GALT3, GALNT6, B3GNT2, GALNT14, FUT11, B3GNT4, GCNT7, B3GNT6, ST6GALNAC1, GALNT3, FUT3, B3GNT3, FUT6, GALNT5, GALNT4, B3GNT5, GALNT12, GCNT1, GALNT7, B4GALT4, and B4GALT1. In some embodiments, mesothelioma is diagnosed by upregulation (e.g., 1-3 fold) of B3GNT9, GALNT9, GALNT13, ST3GAL4, ST3GAL1, B4GALT2, B3GNT7, GALNT12, GALNT2, CHST4, C1GALNT1, GALNT10, GALNT1, and B4GALT4, and downregulation (e.g., 1-3 fold) of GALNT8, B3GNT6, FUT2, FUT1, ST6GALNAC1, GALNT3, FUT3, B3GNT3, FUT6, and GCNT3.

In some embodiments, liver cancer is diagnosed by upregulation (e.g., 1-3 fold) of ST3GAL6, ST3GAL1, ST6GAL1, FUT6, GCNT3, GALNT2, FUT5, CHST4, and GCNT4 and downregulation (e.g., 1-3 fold) of B3GNT9, GALNT9, FUT9, CHST2, GALNT8, FUT10, GALNT6, GALNT14, FUT11, B3GNT4, GALNT3, GALNT12, GCNT1, GALNT7, GALNT10, and B4GALT5. In some embodiments, kidney cancer is diagnosed by upregulation (e.g., 1-3 fold) of GALNT9, GALNT11, B3GNT1, GCNT2, GALNT14, FUT11, B3GNT4, FUT6, GCNT3, GALNT2, FUT5, CHST4, and GCNT4 and downregulation (e.g., 1-3 fold) of B4GALT2, B4GALT3, B3GNT7, GALNT6, B3GNT6, FUT2, ST6GALNAC1, GALNT3, GCNT1, GALNT7, GALNT10, and B4GALNT5.

In some embodiments, testicular germ cell tumor is diagnosed by upregulation (e.g., 1-3 fold) of FUT7, CHST2, ST3GAL2, GALNT8, FUT10, FUT14, ST6GAL1, GCNT2, B3GNT7, GALNT6, B3GNT4, ST6GALNAC1, GCNT1, CHST4, C1GALT1, and downregulation (e.g., 1-3 fold) of FUT9, GALNT11, ST3GAL3, B3GNT1, FUT11, B3GNT6, GALNT3, FUT3, B3GNT3, FUT6, GALNT5, GALNT4, B3GNT5, GALNT1, and GCNT4. In some embodiments, diffuse large B-cell lymphoma is diagnosed by upregulation (e.g., 1-3 fold) of FUT7, CHST2, ST3GAL2, ST6GAL1, and downregulation (e.g., 1-3 fold) of B3GNT9, GALNT9, GALNT13, FUT9, GALNT11, ST3GAL3, B3GNT1, ST3GAL6, ST3GAL4, B4GALT2, FUT10, FUT11, B3GNT4, FUT2, FUT1, B3GNT8, ST6GALNAC1, GALNT3, FUT3, B3GNT3, FUT6, GALNT5, GALNT4, B3GNT5, GALNT7, GALNT2, FUT5, GALNT10, B4GALT5, B4GALT4, and GCNT4.

In some embodiments, thymoma is diagnosed by upregulation (e.g., 1-3 fold) of GALNT9, FUT7, CHST2, GALNT2, and B4GALT4, and downregulation (e.g., 1-3 fold) of B3GNT9, ST3GAL4, ST3GAL1, B4GALT2, GCNT2, B3GNT2, GALNT14, FUT11, B3GNT4, B3GNT6, B3GNT8, ST6GALNAC1, GALNT3, FUT3, B3GNT3, FUT6, GALNT5, GALNT4, B3GNT5, C1GALT1C1, C1GALT1, GALNT10, B4GALT5, GALNT1, and B4GALT4. In some embodiments, STOPH is diagnosed by upregulation (e.g., 1-3 fold) of FUT10, FUT4, B3GNT7, GALNT6, FUT11, GCNT7, B3GNT6, FUT2, B3GNT8, ST6GALNAC1, GALNT3, FUT3, B3GNT3, FUT6, GCNT3, GALNT5, GALNT4, B3GNT5, C1GALT1C1, GCNT1, GALNT7, CHST4, C1GALT1, B4GALT5, and GCNT4 and downregulation (e.g., 1-3 fold) of GALNT9, GALNT11, ST3GAL3, B3GNT1, ST3GAL6, ST3GAL4, and GALNT14.

In some embodiments, colorectal cancer is diagnosed by upregulation (e.g., 1-3 fold) of GALNT8, FUT4, GALNT6, B3GNT6, FUT2, B3GNT8, ST6GALNAC1, GALNT3, FUT3, B3GNT3, FUT6, GCNT3, GALNT5, GALNT4, B3GNT5, C1GALT1C1, GCNT1, GALNT7, C1GALT1, and B4GALT4, and downregulation (e.g., 1-3 fold) of CHST1, B3GNT9, GALNT13, FUT9, GALNT11, ST3GAL3, B3GNT1, ST3GAL6, ST3GAL1, CHST2, GCNT2, GALNT14, FUT11, and GCNT4. In some embodiments, pheochromocytoma and paraganglioma is diagnosed by upregulation (e.g., 1-3 fold) of CHST1, B3GNT9, GALNT13, FUT9, GALNT11, ST3GAL3, B3GNT1, ST3GAL6, ST3GAL2, B3GNT7, GALNT6, B3GNT2, GALNT14, B3GNT14, and C1GALT1C1, and downregulation (e.g., 1-3 fold) of ST3GAL1, B4GALT2, FUT10, FUT4, ST6GAL1, GCNT2, B3GNT6, ST6GALNAC1, GALNT3, FUT3, B3GNT3, FUT6, GCNT3, GALNT5, GALNT4, B3GNT5, GCNT1, GALNT7, GALNT2, FUT5, CHST4, C1GALT1C1, GALNT10, B4GALT5, GALNT1, B4GALT1, and GCNT4.

In some embodiments, glioma is diagnosed by upregulation (e.g., 1-3 fold) of CHST1, GALNT9, GALNT13, FUT9, ST3GAL3, B3GNT1, ST3GAL6, CHST2, GALNT8, and FUT5, and downregulation (e.g., 1-3 fold) of ST3GAL1, FUT7, FUT4, B4GALT3, B3GNT7, GALNT6, B3GNT2, FUT2, FUT1, B3GNT8, GALNT3, FUT3, B3GNT3, FUT6, GCNT3, GALNT5, GALNT4, B3GNT5, GCNT1, GALNT7, CHST4, B4GALT4, and B4GALT1. In some embodiments, uveal melanoma is diagnosed by upregulation (e.g., 1-3 fold) of ST3GAL3, B3GNT1, ST3GAL6, ST3GAL4, ST3GAL1, ST3GAL2, GCNT2, B4GALT3, GALNT14, and downregulation (e.g., 1-3 fold) of CHST1, B3GNT9, GALNT13, FUT9, FUT7, CHST2, GALNT8, FUT4, ST6GAL1, GALNT6, B3GNT2, B3GNT4, GCNT7, B3GNT6, FUT2, FUT1, B3GNT8, ST6GALNAC1, FUT3, B3GNT3, FUT6, GCNT3, GALNT5, GALNT4, B3GNT5, C1GALT1C1, GCNT1, GALNT7, FUT5, CHST4, C1GALT1, GALNT10, B4GALNT5, GALNT1, B4GALT4, B4GALT1, and GCNT4.

In some embodiments, skin cancer (e.g., cutaneous melanoma) is diagnosed by upregulation (e.g., 1-3 fold) of ST3GAL3, B3GNT1, ST3GAL6, ST3GAL4, B4GALT2, ST3GAL2, GCNT2, GALNT2, and downregulation (e.g., 1-3 fold) of B3GNT9, GALNT9, GALNT13, FUT9, GALNT8, FUT4, GALNT6, GALNT14, B3GNT6, FUT2, FUT1, B3GNT8, ST6GALNAC1, FUT3, B3GNT3, FUT6, GCNT3, GALNT4, B3GNT5, GALNT12, C1GALT1C1, GCNT1, GALNT7, FUT5, CHST4, GALNT10, GALNT1, B4GALT4, B4GALT1, and GCNT4.

In all disclosed embodiments, upregulation or downregulation is determined by comparing expression levels of the disclosed genes, to the levels in control (i.e., non cancerous) samples from the same organ/tissue type.

The studies also showed that the expression profile of OGFGTs is associated with patients' survival profiles in glioblastoma multiforme (GBM), indicating clinical their relevance in prognosis and diagnosis in these cancer patients.

OGFGTs were able to separate the glioblastoma samples into two major groups in line with their clinical annotation (IDHwt and IDHmut), and can thus be used to distinguish between these glioblastoma types. The data in the examples demonstrate that IDHwt up-regulated FUT4 while IDHmut up-regulated FUT9, FUT3, FUT6, FUT5, FUT2 and FUT1. More aggressive forms of IDHwt shows upregulation of α2,3-STs such as ST3GAL1, ST3GAL2 and ST3GAL4 while, on the other hand, the less invasive IDHmut samples up-regulated α2,6-STs such as ST6GALNAC. Further, the IDHmut cluster could be classified further into 3 clusters: two corresponding to IDHmut-non-code1 while the third corresponding to IDHmut-code1. OGFGT genes clustered the samples into 4 clusters (G1-4) depending on OGFGT expression. IDHwt samples were low in gene cluster one but high in cluster two while, in contrast, IDHmut samples were high in gene cluster one and low in cluster two. Moreover, IDHmut-code1 can be distinguished from IDHmut-non-code1 by genes in clusters two and four.

IDHwt gravitated towards low expression of a number of fucosyltransferase (FUT) genes. Moreover, although the IDHmut-code1 and the IDHmut-non-code1 subtypes have the same general trend regarding OGFGT gene expression, they can be differentiated by a number of genes including FUT5, GCNT2, B4GALT2, ST3GAL3, FUT4 and B3GNT5.

The OGFGT-based consensus clustering exposed a novel risk group (cluster two) that indicated significantly less survival probability than cluster three and four. This previously unidentified risk group corresponded to the IDHmut-non-code1 and IDHmut-code1 GBM subtypes.

C. Comparison to a Reference

The disclosed methods provide for determining the expression levels of a plurality of O-glycan-forming glycosyltransferases (OGFGTs) in a sample from the subject, and comparing the expression level of each OGFGT in the sample to a reference level. The sample may be compared to a reference sample that is known or suspected to be normal. A normal sample is that which is or is expected to be free of any cancer, disease, or condition, or a sample that would test negative for any cancer disease or condition in the profiling assay. In specific embodiments, a normal sample is a non-cancerous sample and vice versa. The normal sample may be from a different individual from the one being tested, or from the same individual. A normal reference can also represent a value (e.g., median, mean) derived from a population of normal individuals (e.g., samples obtained from these individuals).

By comparison to a normal reference sample, it is possible to determine whether the sample being evaluated is normal or cancerous. For example, if globally, the gene (e.g., OGFGT) expression levels in the test sample deviate from the normal sample, this is suggestive of a cancerous sample. Alternatively, the gene expression levels in the test sample may deviate from the normal sample similarly to how a known cancerous sample deviates from the normal sample. This similarity or concordance between the test sample and the known cancerous sample is suggestive that the test sample is cancerous.

In some embodiments, the reference can be a cancerous sample from the subject, or one or more different subjects. A cancerous sample is a sample that is expected or known to contain tumor or cancer cells or tissue. A cancerous sample would test positive for a marker or indicator of tumor/cancer in a profiling assay. In some embodiments, a cancerous reference can represent a value (e.g., median, mean) derived from a population of individuals having a cancer (e.g., cancerous samples obtained from these individuals). In some embodiments, the reference can be from a database, such as normal or cancer data from The Cancer Genome Atlas, The Genotype-Tissue Expression (GTEx) project, or other published datasets.

By comparison to a cancerous reference sample, it is possible to determine whether the sample being evaluated is normal or cancerous, and if cancerous, what subtype. For example, if globally, the gene (e.g., OGFGT) expression levels in the test sample deviate from the cancer sample, this can be suggestive that the test sample is not cancerous. In some embodiments, if globally, the gene (e.g., OGFGT) expression levels in the test sample deviate from the cancer sample, this can be suggestive that the test sample is of a different type and/or subtype of cancer. Alternatively, the gene expression levels in the test sample may be determined to be similar to the cancerous sample. This can be suggestive that the test sample is of the same type and/or subtype of cancerous reference sample. In some embodiments, the gene (e.g., OGFGT) expression levels in the test sample can deviate from the cancerous reference sample similarly to how a known cancerous sample deviates from the cancerous reference sample. This similarity or concordance between the test sample and the known cancerous sample is suggestive that the test sample is of the same type and/or subtype of cancer.

The OGFGT expression levels in the subject's sample can be determined to be the same, below, or above the reference levels. The comparison can be qualitative or quantitative. The OGFGT expression levels in the subject's sample may or may not be significantly different from the reference levels. In some embodiments, a specified statistical confidence level may be determined in order to provide a diagnostic confidence level. For example, it may be determined that a confidence level of greater than 90% may be a useful predictor of malignancy. In other embodiments, more or less stringent confidence levels may be chosen. For example, a confidence level of approximately 70%, 75%, 80%, 85%, 90%, 95%, 97.5%, 99%, 99.5%, or 99.9% may be chosen as a useful phenotypic predictor. In some embodiments, such as the models used in the Examples, a predictive accuracy of the model or model performance of approximately 90%, 95%, 97.5%, 99%, 99.5%, or 99.9% may be chosen as a useful phenotypic predictor. The confidence level provided may in some cases be related to the quality of the sample, the quality of the data, the quality of the analysis, the specific methods used, and the number of gene expression products analyzed. The specified confidence level for providing a diagnosis may be chosen on the basis of the expected number of false positives or false negatives and/or cost. Methods for choosing parameters for achieving a specified confidence level or for identifying markers with diagnostic power include but are not limited to Receiver Operator Curve analysis (ROC), binormal ROC, principal component analysis, partial least squares analysis, singular value decomposition, least absolute shrinkage and selection operator analysis, least angle regression, and the threshold gradient directed regularization method.

D. Biological Samples

The methods provide for obtaining a sample from a subject. The expression level of OGFGTs are determined in a suitable sample collected from the subject, for example, tissue biopsy samples. The methods of obtaining include methods of biopsy including fine needle aspiration, core needle biopsy, vacuum assisted biopsy, incisional biopsy, excisional biopsy, punch biopsy, shave biopsy or skin biopsy. The sample may be obtained by methods known in the art such as the biopsy methods provided herein, swabbing, scraping, phlebotomy, or any other methods known in the art. The sample may be obtained from any tissue including but not limited to skin, heart, lung, kidney, breast, pancreas, liver, muscle, smooth muscle, bladder, gall bladder, colon, intestine, brain, prostate, esophagus, or thyroid. In some embodiments, a medical professional may obtain a biological sample for testing. In some cases the medical professional may refer the subject to a testing center or laboratory for submission of the biological sample. In other cases, the subject may provide the sample.

In some embodiments, the sample may be obtained, stored, or transported using components of a kit. In some embodiments, multiple samples such as one or more samples from one tissue type (e.g. liver) and one or more samples from another tissue (e.g. lung) may be obtained at the same or different times. The samples obtained at different times can be stored and/or analyzed by different methods. For example, a sample may be obtained and analyzed by cytological analysis (routine staining). In some cases, further sample may be obtained from a subject based on the results of analysis. The diagnosis of cancer may include an examination of a subject by a physician, nurse or other medical professional. The examination may be part of a routine examination, or the examination may be due to a specific complaint including but not limited to one of the following: pain, illness, anticipation of illness, presence of a suspicious lump or mass, a disease, or a condition. The subject may or may not be aware of the disease or condition. The medical professional may obtain a biological sample for testing. In some cases the medical professional may refer the subject to a testing center or laboratory for submission of the biological sample.

A sample suitable for use may be any material containing tissues, cells, nucleic acids, genes, gene fragments, expression products, gene expression products, or gene expression product fragments of an individual to be tested. A sample may include but is not limited to, tissue, cells, or biological material from cells or derived from cells of an individual. The sample may be a heterogeneous or homogeneous population of cells or tissues. The biological sample may be obtained using any method known to the art that can provide a sample suitable for the analytical methods described herein.

The sample may be obtained by non-invasive methods including but not limited to, scraping of the skin or cervix or swabbing of the cheek. In other cases, the sample is obtained by an invasive procedure including but not limited to: biopsy, alveolar or pulmonary lavage, needle aspiration, or phlebotomy. The method of biopsy may further include incisional biopsy, excisional biopsy, punch biopsy, shave biopsy, or skin biopsy. The method of needle aspiration may further include fine needle aspiration, core needle biopsy, vacuum assisted biopsy, or large core biopsy. In some embodiments, multiple samples may be obtained by the methods herein to ensure a sufficient amount of biological material.

The sample can be stored a time such as seconds, minutes, hours, days, weeks, months, years or longer after the sample is obtained and before the sample is analyzed. A portion of the sample may be stored while another portion of said sample is further manipulated. Such manipulations may include but are not limited to molecular profiling; cytological staining; nucleic acid (RNA or DNA) extraction, detection, or quantification; gene expression product (RNA or Protein) extraction, detection, or quantification; fixation; and examination. The sample may be fixed prior to or during storage by any method known to the art such as using glutaraldehyde, formaldehyde, or methanol. The acquired sample may be placed in a suitable medium, excipient, solution, or container for short term or long term storage. Said storage may require keeping the sample in a refrigerated, or frozen environment. The sample may be quickly frozen prior to storage in a frozen environment. The frozen sample may be contacted with a suitable cryopreservation medium or compound including but not limited to: glycerol, ethylene glycol, sucrose, or glucose. A suitable medium, excipient, or solution may include but is not limited to:

hanks salt solution, saline, cellular growth medium, an ammonium salt solution such as ammonium sulphate or ammonium phosphate, or water.

III. Methods

Methods for screening, diagnosis, prognosis and/or treatment of cancer are described. The methods are based on at least determining the expression levels of O-glycan-forming glycosyltransferases (OGFGTs) from a sample in a subject. The methods generally include determining the expression levels of a plurality of OGFGTs in a sample from the subject, comparing the expression level of each OGFGT in the sample to a reference level, and identifying the subject as having a cancer if the expression levels of the plurality of OGFGTs corresponds to an expression signature that is indicative of having the cancer. The described methods and compositions may be used for screening for, diagnosing, providing prognosis, and/or treatment of any type of cancer.

A. Subjects

A subject may be a mammal, such as a domestic animal, farm animal, laboratory animals, non-human primate, or a human Preferably, the subject is a human. The subject may be a human of any age (e.g., 20-80 years). The subject may have a desire or a need to know whether the subject has or is at risk of having a cancer, or is in need of a diagnosis, or prognosis or response to treatment for cancer. The subject may have one or more symptoms of a particular cancer or may be asymptomatic. In some cases, the subject has a prior history of having cancer, including a prior history of having lung, breast, kidney, or brain cancer.

In cases where a subject has one or more symptoms of a cancer, the subject's DNA may be used in methods and/or with compositions of the disclosure. In specific cases, the subject has one or more symptoms such as swelling of all or part of the breast, skin irritation or dimpling, breast pain, nipple pain or the nipple turning inward, redness, scaliness, or thickening of the nipple or breast skin, a nipple discharge other than breast milk, a lump in the underarm area, weight loss, fatigue, anemia, low back pain or pressure on one side, swelling of the ankles and legs, blood in urine, unexplained nausea or vomiting, blurred vision, double vision or loss of peripheral vision headaches, and a combination thereof.

The subject may undergo one or more additional assays for determining presence of cancer in addition to the methods and/or compositions of the disclosure. The additional assay can be performed before, at the same time as, or after performance of the disclosed method for cancer diagnosis and/or prognosis. Exemplary assays include blood tests, mammography, non-invasive imaging, tissue biopsy, HER2 testing, and hormone status testing. Although any other assay may be employed, in some cases the one or more additional assays include ONCOTYPE® (Genomic Health, Inc., Redwood City, CA), HER2 status, MAMMAPRINT® (Agendia BV LLC, Amsterdam, Netherlands), hormone receptor status, carcinoembryonic antigen (CEA) tests, and combinations thereof. The additional assays may be used to identify for example, whether there is a tumor in the breast of the subject, the size of the tumor, and the cancer may be identified at that time.

In specific embodiments, the subject may have a personal or family history of one or more cancers. The disclosed methods may be employed, for example, as a part of routine screening of the subject or may be employed upon indication that the subject has or is at risk for having a cancer or is in need of prognosis, response to treatment, recurrence survey, typing and/or staging of cancer.

B. Screening Subjects

Screening of a subject may be performed as part of a regular checkup or physical examination. Therefore, in certain aspects the subject has not been diagnosed with cancer, and it is unknown whether the subject has a hyperproliferative disorder, such as a breast neoplasm. In other aspects, the subject is at risk of having cancer, is suspected of having cancer, or has a personal or family history of cancer. In some cases, the subject is known to have cancer and is screened as disclosed to determine the type or subtype of cancer, staging of the cancer, treatment response to the cancer, and/or cancer disease prognosis.

C. Diagnosing Subjects

Methods and compositions suitable for cancer screening, diagnosis, and/or prognosis are provided. The methods include assaying expression levels of a plurality of OGFGTs, which may be referred to herein as "markers" or "biomarkers." As used herein, the term "biomarker" or "marker" refers to a substance, molecule, or compound that is produced by, synthesized, secreted, or derived, at least in part, from the cells of the subject and is used to determine presence or absence of a disease, and/or the severity of the disease.

In some embodiments, the diagnosis method is used for diagnosing a cancer including, but not limited to, breast cancer, lung cancer, bladder cancer, liver cancer, or brain cancer, e.g., in biopsy or surgical samples, or in cells from breast, lung, bladder, liver or brain in a bodily fluid such as blood or urine. In some embodiments, the sample is a tissue sample for which a diagnosis is ambiguous (e.g., not clear whether cancerous). In some embodiments, the sample is a tissue sample that upon pathological or other preliminary analysis indicated a diagnosis of no cancer, for which the disclosed compositions, methods, kits, etc. may be used to either confirm the diagnosis of no cancer or to indicate the subject (e.g., patient) has cancer or has an increased likelihood of cancer. In some embodiments, the sample is a bodily fluid or waste sample for which the disclosed compositions, methods, kits, etc. may be as a screen to indicate the patient (e.g., apparently healthy patient, patient suspected of having cancer, patient at increased risk of cancer) has cancer or has an increased likelihood of cancer.

The presence of a particular gene expression signature in the sample from the subject is suggestive of the presence of a particular type or subtype of cancer. The diagnosis of cancer may be divided into malignant or benign. The diagnosis may also be provided such as cancer or level of severity, the likelihood of an accurate diagnosis (such as by a value P, the corrected value P or statistical confidence indication) rating. In some cases, the diagnosis result may indicate a particular type of cancer, a disease or condition, such as liver or lung cancer or any disease or condition provided herein. In some cases, the diagnosis can be indicative of a particular stage of cancer, a disease or condition. Specific information or therapeutic intervention in cancer diagnosis can be given a specific disease or condition for the diagnosis of the type or stage.

In specific embodiments, a subject is diagnosed as having breast, liver, kidney, or brain cancer. In specific embodiments, when a subject is diagnosed as having breast cancer, the subject has breast cancer stage 0, 1, 2, 3, or 4. In specific embodiments, when a subject is diagnosed as having brain cancer such as GBM, the subject has IDH wild type or IDH mutant GBM. In certain embodiments, following a positive diagnosis for a cancer, the subject is treated for that cancer. Treatment for cancer may include surgery, chemotherapy, radiation, gene therapy or a combination thereof.

The disclosed methods assist in accurate tumor diagnosis regardless of the stage of cancer, including the early stages. The methods of the disclosure allow an increase in the overall survival of cancer patients by accurately diagnosing or detecting cancer at early stages and thereby contributing to reducing the cost of patients supported by health authorities.

D. Prognosis of Subjects

Also disclosed are methods for the prognosis of cancer. Prognosis may relate to the disease course, disease duration, and/or expected survival time. In some embodiments, the subject is determined as having a negative prognosis for survival. In some embodiments, the subject is determined as having a positive prognosis for survival.

In some embodiments, the disclosed methods including determining gene expression levels of a plurality of OGFGTs can diagnose a type or subtype of cancer and can predict the degree of aggression of a cancer and risk of recurrence after treatment (e.g., surgical removal of cancer tissue, chemotherapy and radiation therapy, etc.).

In some embodiments, determining the expression of OGFGT genes in a tumor sample from a patient diagnosed of prostate cancer, lung cancer, liver cancer, kidney cancer or brain cancer, predicts the prognosis of the cancer. In some embodiments, a OGFGT gene expression signature indicates a poor prognosis or an increased likelihood of recurrence of cancer in the patient, or a good prognosis or a low likelihood of recurrence of cancer in the patient.

In some embodiments, a subject is prognosticated based on the type or subtype of cancer with which they are diagnosed. For example, in some embodiments, a patient diagnosed with the IDH wild type form of GBM is determined as having a negative prognosis for survival (e.g., compared to a patient having a IDH mutant form). In some embodiments, a patient diagnosed with the IDH mutant form of GBM is determined as having a positive prognosis for survival (e.g., compared to a patient having an IDH wild type form). The disclosed methods may also involve discontinuing administration of current therapy in favor of an alternate therapy, based on the cancer diagnosis and/or prognosis.

E. Treatment of Cancer

Subjects diagnosed with cancer, or having prognosis of cancer and their treatment outcome, may receive therapeutic treatment and care. Accordingly, the disclosed methods can additionally include providing one or more anti-cancer treatments to the subject. For example, disclosed is a method for cancer diagnosis and/or prognosis of a subject by (a) determining the expression levels of a plurality of OGFGTs in a sample from the subject; (b) comparing the expression level of each OGFGT in the sample to a reference level; (c) identifying the subject as having a cancer if the expression levels of the plurality of OGFGTs corresponds to an expression signature that is indicative of having the cancer; and (d) providing anti-cancer treatment to the subject for the cancer. The specific anti-cancer treatment used can based upon the diagnosis and/or prognosis. As another example, disclosed is a method for treating cancer in a subject by (a) determining the expression levels of a plurality of OGFGTs in a sample from the subject; (b) comparing the expression level of each OGFGT in the sample to a reference level; (c) identifying the subject as having a cancer if the expression levels of the plurality of OGFGTs corresponds to an expression signature that is indicative of having the cancer; and (d) providing anti-cancer treatment to the subject for the cancer. The specific anti-cancer treatment used can based upon the diagnosis and/or prognosis.

The therapeutic treatment and care may be anti-cancer treatment and care. The therapeutic treatment and care may be the same as the treatment and care the subject may have received prior to diagnosis and/or prognosis, or different from the treatment and care that the subject may have received prior to diagnosis and/or prognosis.

In some embodiments, the treatment is specific to the cancer with which the subject is diagnosed. For example, a subject diagnosed with lung cancer may be administered a chemotherapeutic agent that is specifically approved for treatment of and/or administered for lung cancer. As another example, diagnosing a subject as having glioblastoma can inform treatment based on the identification of the GBM subtype. For instance, treatment for IDH-wild type GBM is distinct from that of the IDH-mut GBM, and IDH-mut co-del GBM has a more favorable prognosis and is more likely to respond to treatment relative to the IDH-mut with non-co-del GBM.

The disclosed methods allow one to characterize how tumor cells are distinct from normal cells of the same tissue, and then design or select therapies that can target those specific features only. The disclosed methods also allow for identification of similarities and differences across cancer types, for drug repurposing or for transfer of knowledge from a well-studied cancer type to a less-studied one. For example, identification of a previously unknown similarity between two distinct cancer types based on the OGFGT expression profiling, may suggest that therapies used in one cancer are likely to be successful in the second cancer.

i. Anti-Cancer Treatments

Exemplary anti-cancer treatments include surgery, chemotherapy, radiation therapy, immunotherapy, gene therapy, targeted therapy, stem cell transplant, or combinations thereof. Chemotherapy may include a treatment with an effective amount of an anti-cancer/chemotherapeutic agent. Accordingly, in some embodiments of the disclosed methods of diagnosis, prognosis, and/or treatment, a subject is administered an effective amount of one or more chemotherapeutic agents. Exemplary chemotherapeutic agents that can be used include, without limitation, Azacitidine; Capecitabine; Carmofur; Cladribine; Clofarabine; Cytarabine; Decitabine; Floxuridine; Fludarabine; Fluorouracil; Gemcitabine; Mercaptopurine; Nelarabine; Pentostatin; Tegafur; Methotrexate; Daunorubicin; Doxorubicin; Epirubicin; Docetaxel; Paclitaxel; Vinblastine; Vincristine; Cisplatin, etc.

Numerous antineoplastic drugs are available for use in the disclosed methods. In some embodiments, the one or more therapeutics is a chemotherapeutic or antineoplastic drug. The majority of chemotherapeutic drugs can be divided into alkylating agents, antimetabolites, anthracyclines, plant alkaloids, topoisomerase inhibitors, monoclonal antibodies, and other antitumour agents.

Other exemplary anti-cancer/chemotherapeutic agents that can be used in accordance with the disclosed methods include, but are not limited to, gefitinib, erlotinib, cis-platin, 5-fluorouracil, tegafur, raltitrexed, cytosine arabinoside, hydroxyurea, adriamycin, bleomycin, daunomycin, mitomycin-C, dactinomycin and mithramycin, vincristine, vinblastine, vindesine, vinorelbine, etoposide, etoposide phosphate, teniposide, camptothecins such as irinotecan and topotecan, camptothecin bortezomib anegrilide, tamoxifen, toremifene, raloxifene, droloxifene, iodoxyfene fulvestrant, bicalutamide, flutamide, nilutamide, cyproterone, goserelin, leuprorelin, buserelin, megestrol, anastrozole, letrozole, vorazole, exemestane, finasteride, marimastat, dacarbazine, oxaliplatin, procarbazine, temozolomide, valrubicin, actinomycins such as actinomycin D, trastuzumab (HERCEPTIN®), bevacizumab (AVASTIN®), gemtuzumab (MYLOTARG®), panitumumab (VECTIBIX®) or edrecolomab (PANOREX®), tyrosine kinase inhibitor, such as sorafenib (NEXAVAR®) or sunitinib (SUTENT®), cetuximab, dasatinib, imatinib, combretastatin, thalidomide, and/or lenalidomide, alkylating agents; alkyl sulfonates; aziridines, such as Thiotepa; ethyleneimines; anti-metabolites; folic acid-analogues, such as methotrexate (FARMITREXAT®, LANTAREL®, METEX®, MTX HEXAL®); purine analogues, such as azathioprine (AZAIPRIN®, AZAMEDAC®, IMUREK®, Zytrim®), cladribin (LEU-STATIN®), fludarabin phosphate (Fulda®), mercapto purine (MERCAP®, PURI-NETHOL®), pentostatin (NIPENT®), thioguanine (THIOGUANIN-WELLCOME®) or fludarabine; pyrimidine analogues, such as cytarabin (ALEXAN®, ARA-CELL®, UDICIL®), fluorouracil, 5-FU (EFUDIX®, FLUOROBLASTIN®, RIB OFLUOR®), gemcitabine (GEMZAR®), doxifluridine, azacitidine, carmofur, 6-azauridine, floxuridine; nitrogen-lost-derivatives, such as chlorambucil (LEUKERAN®), melphalan (ALKERAN®), chlornaphazine, estramustin, mechlorethamine; oxazaphosphorines, such as cyclophosphamide (CYCLO-CELL®, CYCLOSTIN®, ENDOXAN®), ifosfamide (HOLOXAN®, IFO-CELL®) or trofosfamide (IXOTEN®); nitrosureas, such as Bendamustine (RIB OMUSTIN®), Carmustine (CARMUBRIS®), Fotemustine (MUPHORAN®), Lomustine (CECENU®, LOMEBLASTIN®), chlorozotocine, ranimustine or nimustine (ACNU®); hydroxy-ureas (LITALIR®); taxens, such as docetaxel (TAXOTERE®), or paclitaxel (TAXOL®); platinum-compounds, such as cisplatin (PLATIBLASTIN®, PLATINEX®) or carboplatin (CARBOPLAT®, RIB OCARBO®); sulfonic acid esters, such as busulfan (MYLERAN®), piposulfan or treosulfan (OVASTAT®); anthracyclines, such as doxorubicin (ADRIBLASTIN®, DOXO-Cell®), daunorubicin (DAUNOBLASTIN®), epirubicin (FARMORUBICIN®), idarubicin (ZAVEDOS®), amsacrine (AMSIDYL®) or Mitoxantrone (NOVANTRON®); as well as derivates, tautomers and pharmaceutically active salts of the aforementioned compounds.

The subject can also be treated with one or more targeted cancer therapies. In the context of cancer, targeted therapies are therapeutic agents that block the growth and spread of cancer by interfering with specific molecules ("molecular targets") that are involved in the growth, progression, and spread of cancer. Targeted cancer therapies are sometimes called molecularly targeted drugs, molecularly targeted therapies, or precision medicines. Many different targeted therapies have been approved for use in cancer treatment. These therapies include hormone therapies, signal transduction inhibitors, gene expression modulators, apoptosis inducers, angiogenesis inhibitors, immunotherapies, and toxin delivery molecules. Anti-PD-L1 antibodies and antigen-binding fragments thereof and/or anti-CTLA-4 antibodies (e.g., Ipilimumab and Tremelimumab) and antigen-binding fragments thereof can be administered. Exemplary lung cancer targeted therapies which may be used in accordance with the disclosed compositions and methods include, but are not limited to, Bevacizumab, crizotinib, erlotinib, gefitinib, afatinib dimaleate, ceritinib, ramucirumab, nivolumab, pembrolizumab, osimertinib, necitumumab, alectinib, atezolizumab, brigatinib, trametinib, dabrafenib, and durvalumab.

ii. Cancers to be Treated

Cancer is a disease of genetic instability, allowing a cancer cell to acquire the hallmarks proposed by Hanahan and Weinberg, including (i) self-sufficiency in growth signals; (ii) insensitivity to anti-growth signals; (iii) evading apoptosis; (iv) sustained angiogenesis; (v) tissue invasion and metastasis; (vi) limitless replicative potential; (vii) reprogramming of energy metabolism; and (viii) evading immune destruction (*Cell.,* 144:646-674, (2011)).

Cancers which may be treated in accordance with the disclosed methods can be classified according to the embryonic origin of the tissue from which the cancer is derived. Carcinomas are tumors arising from endodermal or ectodermal tissues such as skin or the epithelial lining of internal organs and glands. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The disclosed compositions and methods of treatment thereof are generally suited for treatment of carcinomas, sarcomas, lymphomas and leukemias. The described compositions and methods are useful for treating, or alleviating subjects having benign or malignant tumors by delaying or inhibiting the growth/proliferation or viability of tumor cells in a subject, reducing the number, growth or size of tumors, inhibiting or reducing metastasis of the tumor, and/or inhibiting or reducing symptoms associated with tumor development or growth.

The types of cancer that can be diagnosed and/or treated with the provided compositions and methods include, but are not limited to, cancers such as vascular cancer, myeloma, adenocarcinomas and sarcomas of bone, bladder, brain, breast, cervical, colorectal, esophageal, kidney, liver, lung, nasopharangeal, pancreatic, prostate, skin, stomach, and uterine. In some embodiments, the compositions and methods are used to treat multiple cancer types concurrently. The compositions and methods can also be used to treat metastases or tumors at multiple locations.

Exemplary tumor cells include, but are not limited to, tumor cells of cancers, including leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as, but not limited to, chronic myelocytic (granulocytic) leukemia, chronic lymphocytic leukemia, hairy cell leukemia; polycythemia vera; lymphomas such as, but not limited to, Hodgkin's disease, non-Hodgkin's disease; multiple myelomas such as, but not limited to, smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including, but not limited to, pheochromocytom and adrenocortical carcinoma; thyroid cancer such as but not limited to papillary or follicular thyroid cancer, medullary thyroid cancer and anaplastic thyroid cancer; pancreatic cancer, including, but not limited to, insulinoma, gastrinoma, glucagonoma, vipoma, somatostatin-secreting tumor, and carcinoid or islet cell tumor; pituitary cancers including, but not limited to, Cushing's disease, prolactin-secreting tumor, acromegaly, and diabetes insipius; eye cancers including, but not limited to, ocular melanoma such as iris melanoma, choroidal melanoma, and ciliary body melanoma, and retinoblastoma; vaginal cancers, including, but not limited to, squamous cell carcinoma, adenocarcinoma, and melanoma; vulvar cancer, including, but not limited to, squamous cell carcinoma, melanoma, adenocarcinoma, basal cell carcinoma, sarcoma, and Paget's disease; cervical cancers including, but not limited to, squamous cell carcinoma, and adenocarcinoma; uterine cancers including, but not limited to, endometrial carcinoma and uterine sarcoma; ovarian cancers including, but not limited to, ovarian epithelial carcinoma, borderline tumor, germ cell tumor, and stromal tumor; esophageal cancers including, but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including, but not limited to, hepatocellular carcinoma and hepatoblastoma, gallbladder cancers including, but not limited to, adenocarcinoma; cholangiocarcinomas including, but not limited to, papillary, nodular, and diffuse; lung cancers including, but not limited to, non-small cell lung cancer, squamous cell carcinoma (epidermoid carcinoma), adenocarcinoma, large-cell carcinoma and small-cell lung cancer; testicular cancers including, but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including, but not limited to, adenocarcinoma, leiomyosarcoma, and rhabdomyosarcoma; penal cancers; oral cancers including, but not limited to, squamous cell carcinoma; basal cancers; salivary gland cancers including, but not limited to, adenocarcinoma, mucoepidermoid carcinoma, and adenoidcystic carcinoma; pharynx cancers including, but not limited to, squamous cell cancer, and verrucous; skin cancers including, but not limited to, basal cell carcinoma, squamous cell carcinoma and melanoma, superficial spreading melanoma, nodular melanoma, lentigo malignant melanoma, acral lentiginous melanoma; kidney cancers including, but not limited to, renal cell cancer, adenocarcinoma, hypernephroma, fibrosarcoma, transitional cell cancer (renal pelvis and/or uterer); Wilms' tumor; bladder cancers including, but not limited to, transitional cell carcinoma, squamous cell cancer, adenocarcinoma, and carcinosarcoma. For a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

In some embodiments, the cancer(s) to be treated is characterized as being a triple negative cancer, or having one or more KRAS-mutations, p53 mutations, EGFR mutations, ALK mutations, RB1 mutations, HIF mutations, KEAP mutations, NRF mutations, or other metabolic-related mutations, or combinations thereof. In preferred embodiments, the cancer to be treated is liver cancer (e.g., hepatocellular carcinoma), kidney cancer (e.g., renal cell carcinoma), breast cancer (e.g. breast invasive carcinoma), lung cancer (e.g., lung adenocarcinoma, lung squamous cell carcinoma), and/or glioblastoma including GBM subtypes such as, IDH wild type, IDH mutant with 1p/19q co-deletion, and IDH mutant without 1p/19q co-deletion.

iii. Effective Amounts

The effective amount or therapeutically effective amount of a disclosed therapeutic agent (e.g., chemotherapeutic agent) can be a dosage sufficient to treat, inhibit, or alleviate one or more symptoms of a disease or disorder, or to otherwise provide a desired pharmacologic and/or physiologic effect, for example, reducing, inhibiting, or reversing one or more of the underlying pathophysiological mechanisms underlying a disease or disorder such as cancer.

In some embodiments, administration of the therapeutic agents (e.g., chemotherapeutic agents) elicits an anti-cancer response, the amount administered can be expressed as the amount effective to achieve a desired anti-cancer effect in the recipient. For example, in some embodiments, the amount of the therapeutic agent is effective to inhibit the viability or proliferation of cancer cells in the recipient. In some embodiments, the amount of therapeutic agent is effective to reduce the tumor burden in the recipient, or reduce the total number of cancer cells, and combinations thereof. In other forms, the amount of the therapeutic agents is effective to reduce one or more symptoms or signs of cancer in a cancer patient. Signs of cancer can include cancer markers, such as PSMA levels in the blood of a patient.

The effective amount of the therapeutic agents required will vary from subject to subject, depending on the species, age, weight and general condition of the subject, the severity of the disorder being treated, and its mode of administration. Thus, it is not possible to specify an exact amount for every therapeutic agent. However, an appropriate amount can be determined by one of ordinary skill in the art using only routine experimentation given the teachings herein. For example, effective dosages and schedules for administering the therapeutic agents can be determined empirically, and making such determinations is within the skill in the art. In some embodiments, the dosage ranges for the administration of the therapeutic agents are those large enough to effect reduction in cancer cell proliferation or viability, or to reduce tumor burden for example.

The dosage should not be so large as to cause adverse side effects, such as unwanted cross-reactions, anaphylactic reactions, and the like. Generally, the dosage will vary with the age, condition, and sex of the patient, route of administration, whether other drugs are included in the regimen, and the type, stage, and location of the disease to be treated. The dosage can be adjusted by the individual physician in the event of any counter-indications. It will also be appreciated that the effective dosage of the composition used for treatment can increase or decrease over the course of a particular treatment. Changes in dosage can result and become apparent from the results of diagnostic assays.

Dosage can vary, and can be administered in one or more dose administrations daily, for one or several days. Guidance can be found in the literature for appropriate dosages for given classes of pharmaceutical products. Optimal dosing schedules can be calculated from measurements of drug accumulation in the body of the subject or patient. Persons of ordinary skill can easily determine optimum dosages, dosing methodologies and repetition rates. Optimum dosages can vary depending on the relative potency of individual pharmaceutical compositions, and can generally be estimated based on $EC_{50}$s found to be effective in in vitro and in vivo animal models.

Dosages can be repeated as often and as many times as the patient can tolerate until the desired response is achieved. The optimal dosage and treatment regime for a particular patient can readily be determined by one skilled in the art of medicine by monitoring the patient for signs of disease and adjusting the treatment accordingly. In some embodiments, the unit dosage is in a unit dosage form for intravenous injection. In some embodiments, the unit dosage is in a unit dosage form for oral administration. In some embodiments, the unit dosage is in a unit dosage form for inhalation. In some embodiments, the unit dosage is in a unit dosage form for intratumoral injection.

Treatment can be continued for an amount of time sufficient to achieve one or more desired therapeutic goals, for example, a reduction of the amount of cancer cells relative to the start of treatment, or complete absence of cancer cells in the recipient. Treatment can be continued for a desired period of time, and the progression of treatment can be monitored using any means known for monitoring the progression of anti-cancer treatment in a patient. In some embodiments, administration is carried out every day of treatment, or every week, or every fraction of a week. In some embodiments, treatment regimens are carried out over the course of up to two, three, four or five days, weeks, or months, or for up to 6 months, or for more than 6 months, for example, up to one year, two years, three years, or up to five years.

The efficacy of administration of a particular dose of the therapeutic agents according to the methods described herein can be determined by evaluating the particular aspects of the medical history, signs, symptoms, and objective laboratory tests that are known to be useful in evaluating the status of a subject in need for the treatment of cancer or other diseases and/or conditions. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular individual: (1) a subject's physical condition is shown to be improved (e.g., a tumor has partially or fully regressed), (2) the progression of the disease or condition is shown to be stabilized, or slowed, or reversed, or (3) the need for other medications for treating the disease or condition is lessened or obviated, then a particular treatment regimen will be considered efficacious. In some embodiments, efficacy is assessed as a measure of the reduction in tumor volume and/or tumor mass at a specific time point (e.g., 1-5 days, weeks or months) following treatment.

iv. Modes of Administration

Therapeutic agents can be administered according to standard procedures used by those skilled in the art. In some embodiments, the therapeutic agents described herein can be conveniently formulated into pharmaceutical compositions composed of one or more of the peptides in association with a pharmaceutically acceptable carrier. See, e.g., *Remington's Pharmaceutical Sciences*, latest edition, by E. W. Martin Mack Pub. Co., Easton, PA, which discloses typical carriers and conventional methods of preparing pharmaceutical compositions that can be used and which is incorporated by reference herein. These most typically would be standard carriers for administration of compositions to humans. In one aspect, for humans and non-humans, these include solutions such as sterile water, saline, and buffered solutions at physiological pH.

Compositions of the therapeutic agents can include carriers, thickeners, diluents, buffers, preservatives, surface active agents and the like in addition to the therapeutic agent of choice.

Therapeutic agents can be administered to a subject in a number of ways depending on whether local or systemic treatment is desired, and on the area to be treated. Thus, for example, a therapeutic agent can be administered to a subject vaginally, rectally, intranasally, orally, by inhalation, or parenterally, for example, by intradermal, subcutaneous, intramuscular, intraperitoneal, intrarectal, intraarterial, intralymphatic, intravenous, intrathecal and intratracheal routes. The therapeutic agents can be administered directly into a tumor or tissue, e.g., stereotactically.

Parenteral administration, if used, is generally characterized by injection. Injectables can be prepared in conventional forms, either as liquid solutions or suspensions, solid forms suitable for solution or suspension in liquid prior to injection, or as emulsions. An approach for parenteral administration involves use of a slow release or sustained release system such that a constant dosage is maintained. See, e.g., U.S. Pat. No. 3,610,795, which is incorporated by reference herein. Suitable parenteral administration routes include intravascular administration (e.g., intravenous bolus injection, intravenous infusion, intra-arterial bolus injection, intra-arterial infusion and catheter instillation into the vasculature); peri- and intra-tissue injection (e.g., intraocular injection, intra-retinal injection, or sub-retinal injection); subcutaneous injection or deposition including subcutaneous infusion (such as by osmotic pumps); direct application by a catheter or other placement device (e.g., an implant comprising a porous, non-porous, or gelatinous material).

Preparations for parenteral administration include sterile aqueous or non-aqueous solutions, suspensions, and emulsions which can also contain buffers, diluents and other suitable additives. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Administration of the therapeutic agents can be localized (i.e., to a particular region, physiological system, tissue, organ, or cell type) or systemic.

IV. Kits

Kits for the detection, characterization, diagnosis of cancer are provided. Any of the compositions described herein may be part of a kit.

The kit may include a carrier for the various components of the kit. The carrier can be a container or support, in the form of, e.g., bag, box, tube, rack, and is optionally compartmentalized. The carrier may define an enclosed confinement for safety purposes during shipment and storage. The kit may generally include at least one vial, test tube, flask, bottle, syringe, or other container means.

The kit may include devices suitable for extraction of a sample from an individual, including by non-invasive means. Such devices include swab (including rectal swab), phlebotomy material(s), scalpel, syringe, rod, and so forth.

The kit can include various components useful in determining the expression levels of one or more genes in accordance with the disclosed methods. In some embodiments, the kits contain reagents specific for the detection of mRNA or cDNA (e.g., oligonucleotide probes or primers). For example, the kit many include oligonucleotides specifically hybridizing to mRNA or cDNA of the OGFGT genes disclosed above. Such oligonucleotides can be used as PCR primers in RT-PCR reactions, or hybridization probes. In some embodiments, the kits contain RNA-sequencing reagents for determining the expression level of OGFGTs. In some embodiments the kit comprises reagents (e.g., probes, primers, and or antibodies) for determining the expression level of a plurality of OGFGTs. In some embodiments, the oligonucleotides in the kit can be labeled with any suitable detection marker including but not limited to, radioactive isotopes, fluorophores, biotin, enzymes (e.g., alkaline phosphatase), enzyme substrates, ligands and antibodies, etc.

In some embodiments, the kits contain antibodies specific for one or more gene products (e.g., OGFGT gene products), in addition to detection reagents and buffers. In preferred embodiments, the kits contain all of the components necessary to perform a detection assay, including all controls, directions for performing assays, and any necessary software for analysis and presentation of results. In some embodiments, the kit includes instructions on using the kit for diagnosis and/or prognosis of cancer.

The following non-limiting examples further explain the disclosed and claimed compositions and methods.

EXAMPLES

Example 1: Comprehensive Gene Expression Analysis of 55 OGFGTs Distinguishes Normal and Cancer Tissue, Cancer Type and Subtype, and Predicts Likelihood of Survival

Materials and Methods

Development of an OGFGT Model Classifier

To develop an OGFGT-based classifier in the domains of neoplastic transformation (cancer vs normal), cancer types and cancer subtypes, a machine learning approach was used to develop a group of models to predict class labels from random samples (FIG. 1A). The RNA sequencing (RNA-Seq) V2 dataset from The Cancer Genome Atlas (TCGA) database was chosen as a candidate for model development since it harbors a high number of patient samples, an availability of normal-matched samples, an availability of survival data, an accessibility to clinical metadata and an availability of a wide range of cancer types. Centering and scaling before being transformed using the Yeo-Johnson transformation method, normalized the normal-matched tumor sample pairs.[29]

External Validation of the Normal-Versus-Tumor Classifier

Figure 4A:
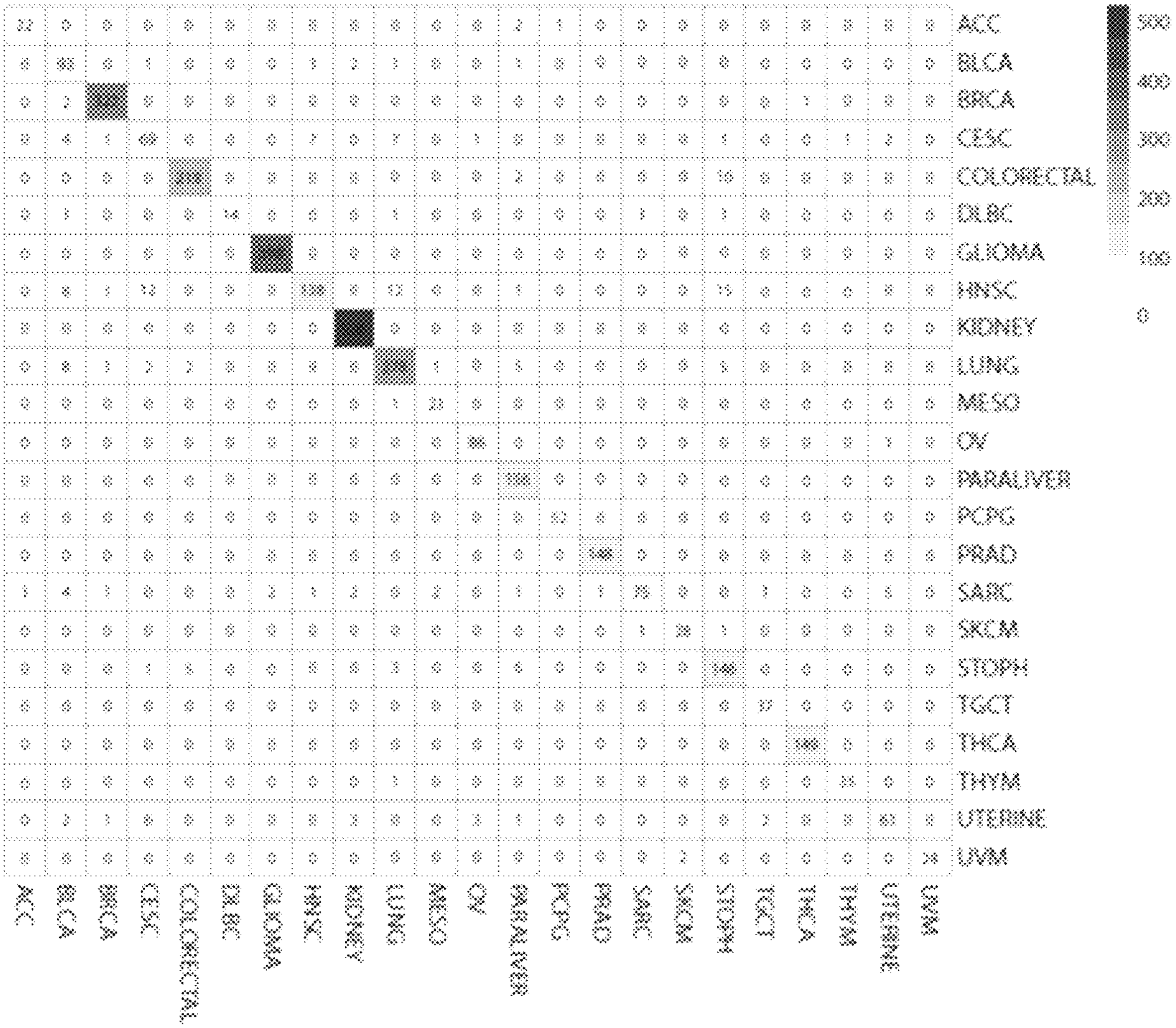
FIG. 4A. Confusion Matrix of the internal validation of the OGFGT-based cancer types classifier. Predictions are in the rows and the truths are in the columns.
Figure 4B:
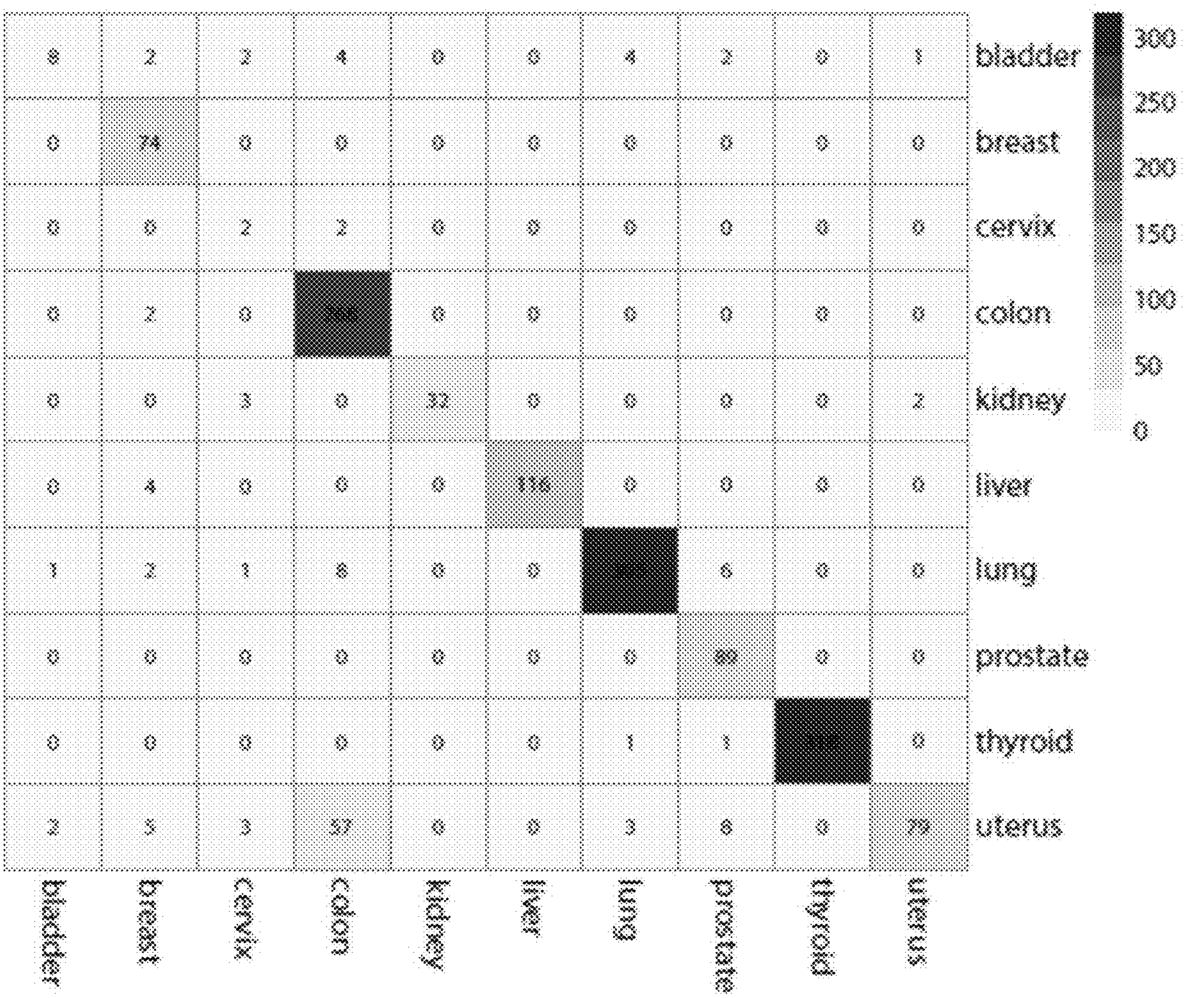
FIG. 4B. Confusion matrix of the prediction of cancer type using OGFGT-based classifier on the GTEx external dataset. Predictions are in the rows and the truths are in the columns Color indicates the number of samples. The number in the diagonal of the confusion matrix indicates the agreement between the prediction and the truth. The off-diagonal numbers indicate the misclassified samples.

To establish the reproducibility of the models, validation was done using an external dataset. The two basic assumptions in traditional machine learning: (1) the training (also referred as source domain) and test data (also referred target domain) should follow the independent and identical distributed (i.i.d.) condition; (2) there are enough labeled samples to learn a good classification model. The second assumption is genuinely fulfilled by the abundant number of samples of the TCGA dataset. However, the first assumption is hardly fulfilled with the conventional normalization methods of the RNA-Seq data. To overcome this problem, a pipeline developed by Wang et al. (PMID: 29664468)[15] that is specifically developed to unify normal and RNA sequencing data from different sources, was used. The TCGA and GTEx data as normalised by the authors was downloaded from https://github.com/mskcc/RNAseqDB. The TCGA dataset was then used for cross validation, while the GTEx dataset was used for the external validation. External validation was done for 10 overlapping cancer types (FIG. 4B).

Development of OGFGT Predictive Model for Glioblastoma Subtype

Seeking more evidence for the ability of the OGFGT genes to classify glioblastoma subtypes, multi-dimensional scaling (MDS) was performed using principal component analysis (PCA) and linear discriminant analysis (LDA). Both analyses showed that the OGFGTs were able to cluster the glioblastoma samples into their respective clinical subtypes where the relative distance between the IDHwt cluster and any of the two mutant clusters is greater than the relative distance between the IDHmut-codel and the IDHmut-non-codel subtypes.

To evaluate the ability of the OGFGT to identify the glioblastoma subtype from a random glioblastoma sample, the RDA method was used to develop a glioblastoma subtype classifier model. The model development outlines in FIG. 1A was followed. Briefly, 658 glioblastoma samples from the TCGA dataset were split into training and testing subsets randomly at a 70/30 rate Manipulating only the training subset, it was preprocessed by removing the near-zero varying features, centering and scaling. To stabilize the dataset and conform it into a normal-like distribution, Yeo-Johnson transformation was performed.[53] The RDA model was tuned using repeated 10-fold cross validation searching a grid of regularization parameters and y for the optimal solution.

Development of OGFGT Based Model Classifier

To test the capability of the OGFGT genes to predict the normal-tumor status and/or the cancer types, three types of predictive models were developed. The first model takes into consideration the normal-tumor status and the cancer type. The second model considers the normal-tumor status in each tumor individually. The third type models the normal-tumor status collectively regardless of the cancer type (FIG. 1B-E).

Figure 1B:
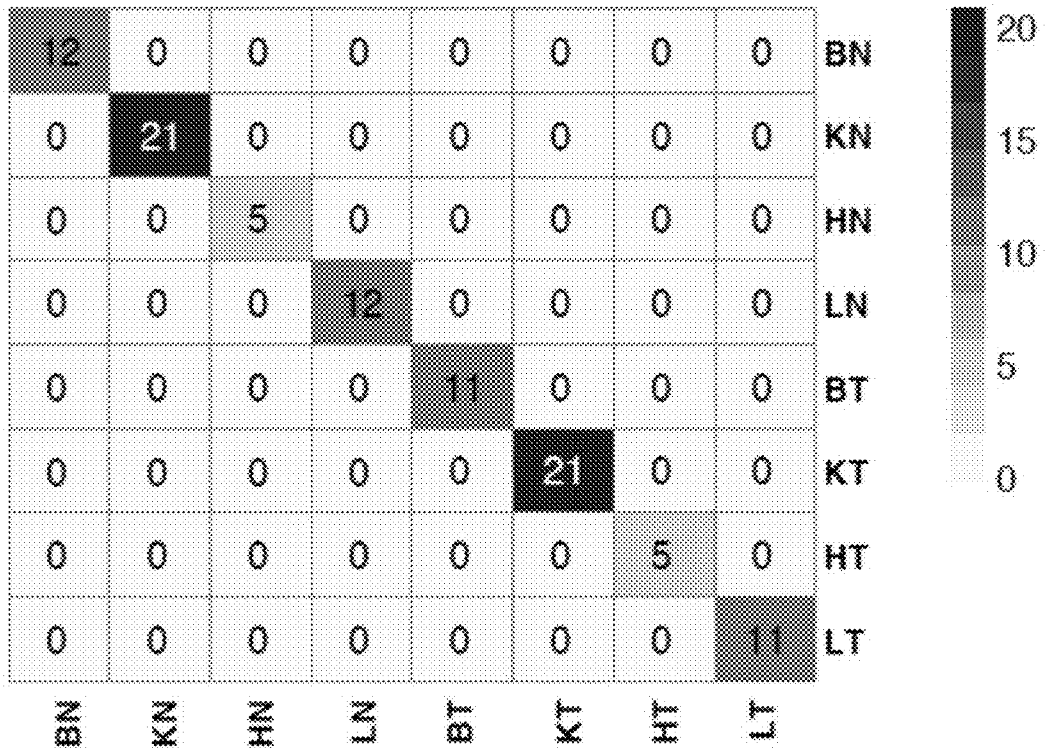
Figure 1C:
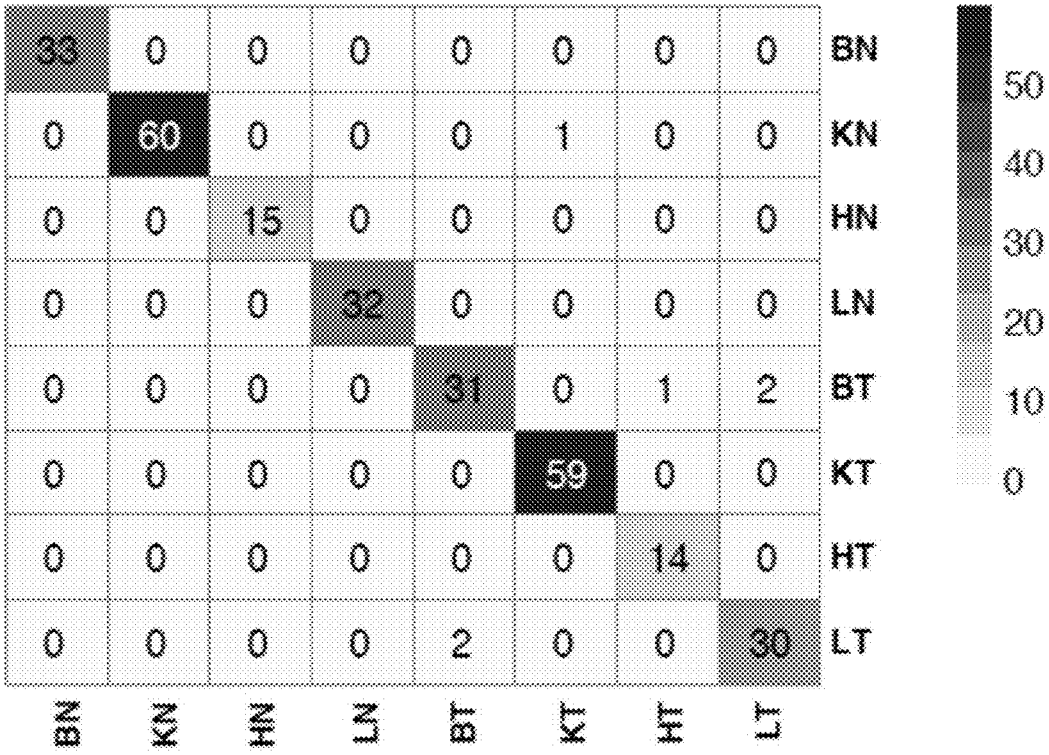

The first classifier was developed to predict the cancer type in addition to the normal/tumor status (FIGS. 1B and C). The confusion matrices of prediction in the 10-fold cross validation and the internal blind testing showed accuracy values of 98.16% and 97.86% respectively. Consequently, the performance metrics of this classifier demonstrated high probabilities of both true detection and true exclusion as well as true labeling of a random samples (FIGS. 1B and C; FIG. 2A).

The normal-tumor classifier in each cancer type was developed on the training subset of six cancer types using the RDA method in leave-one-out cross validation (LOOCV) approach for parameter tuning. Due to the relatively low number of samples, the datasets were split into training and testing at a 50/50 rate (FIG. 1D). The confusion matrices of the prediction of the testing subset of the cancer types showed highly accurate performance of the classifiers (FIG. 1D). The BRCA produced 97.32% accuracy, 100% sensitivity and 94.64% specificity. The KIPAN produced 98.44% accuracy, 98.44% sensitivity and 98.44% specificity. The KIRC produced 97.22% accuracy, 97.22% sensitivity and 97.22% specificity. The LIHC produced 96% accuracy, 100% sensitivity and 92% specificity. The LUAD produced 100% accuracy, 100% sensitivity and 100% specificity. The LUSC produced 98% accuracy, 100% sensitivity and 96% specificity (FIG. 1D).

The normal-tumor classifier regardless of type also demonstrated reliable predictions in the confusion matrices of the 10-fold cross validation and the internal blind testing with accuracy values of 97.08% and 97.86% respectively (FIG. 1E). The classifier showed strong performance metrics of 100% sensitivity, 95.71% specificity, 95.89% positive predictive value (PPV) and 100% negative predictive value (NPV).

Development of OGFGT Based Cancer-Type Model Classifier

To explore the unique expression signature across different cancer types, the expression of each cancer type was summarized by averaging. The matrix of averages showed the differential expression of the OGFGT genes across cancer types. These signatures are the basis for the ability of the OGFGT genes to cluster the samples according to their types. This can be viewed as placing each sample in a spot in the multi-dimensional space of the clustering features. Moreover, this acts as a motive to look for cancer specific prognostic markers and develop models for prediction of cancer types from random samples. Furthermore, the clustering of cancer types based on the OGFGT expression shows distinctive relative distances between different cancer types.

Validation on GTEx Data

Figures 2B, 3B:
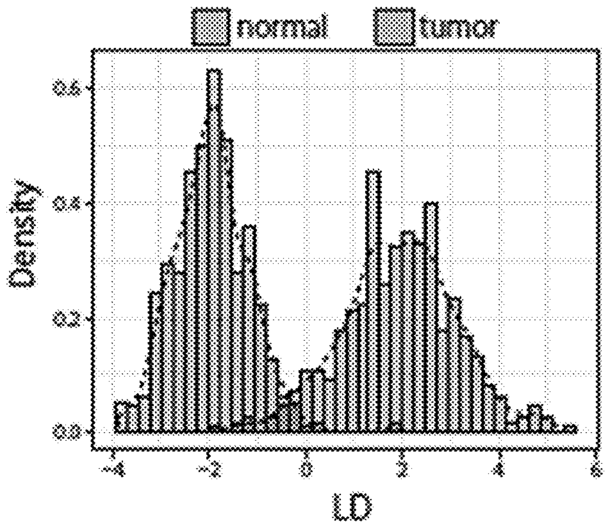
FIG. 2B. LD projections of tumor and matched normal samples treated as two groups (i.e. type label ignored).
FIG. 3B. Performance metrics of the OGFGT-based cancer type classifier on the GTEx external dataset. Sens., sensitivity; Spec., specificity; PPV, positive predictive value; NPV, negative predictive value; F1, F1 score; BA, balanced accuracy.

A significant number of the uterine samples were misclassified as colon (FIG. 4B; FIG. 3B). Although the performance metrics of the bladder and the cervical cancer types were relatively low, this was considered inconclusive due to the low number of samples (FIG. 4B; FIG. 3B).

Results

OGFGTs Expression Signature can Distinguish Cancer from Normal Patient Samples

Compared to normal cells, cancer-associated O-glycans can be highly sialylated and less sulphated; they can be truncated and commonly contain sialylated and unsialylated Tn and T antigens.[14] Several O-glycan GTs are found to exhibit significant changes in their expression profiles among cancer tissues relative to their normal counterparts, yet a systematic view in the global expression profiles of OGFGTs associated with carcinogenesis has not been performed. In order to catalogue and identify the perturbations that occur among OGFGTs in cancer cells relative to their normal counterparts, a model classifier that can distinguish between cancer and non-cancer tissue samples based on the expression profiles of a curated-set of 55 GT genes was developed. To this end, RNA sequencing data from The Cancer Genome Atlas (TCGA) incorporating 6 different cancer types for which tumor and matched-normal samples were available (n=944) breast invasive carcinoma (BRCA, n=224), pan-kidney cohort (KIPAN, n=258), kidney renal cell carcinoma (KIRC, n=144), liver hepatocellular carcinoma (LIHC, n=100), lung adenocarcinoma (LUAD, n=116) and lung squamous cell carcinoma (LUSC, n=102), was used.

Briefly, the development pipeline (FIG. 1A) of the OGFGT-based predictive classifier is based on regularized discriminant analysis (RDA) method where the tuning parameters were optimized through repeated 10-fold cross validation beginning with splitting the dataset into training and testing subsets. The training subset was used for the optimization of the preprocessing and modeling parameters using the repeated k-fold cross validation approach. The predefined set of preprocessing and modeling parameters were then validated on the testing subset for model evaluation of the final stable predictive model.

Unsupervised techniques tend to show the inherited patterns of samples according to the features in hand. Unsupervised hierarchical clustering was thereby performed individually on each cancer type and using the set of 55 OGFGTs, each cancer type was reliably clustered into two distinct groups of normal and tumor samples (FIG. 2A and FIGS. 1B-E). Similarly, the linear discriminant analysis (LDA) of k=1 showed significant separation between the normal and tumor samples across the six cancer types. Importantly, LDA not only illustrated the ability of OGFGT genes to distinguish between normal and tumor samples in each cancer type independently, but it was also able to distinguish between the normal and tumor labels collectively regardless of the cancer type at k=1 discriminant variable (FIG. 2B). Moreover taking into consideration both the normal/tumor label and the cancer type label at k=7 discriminant variables, a cross-correlation network analysis based on LD projections of tumor with their matched normal samples was constructed. OGFGTs were able to distinguish between the different tissue types (i.e. liver, kidney, breast, lung) as well as between the cancer and the non-cancer samples within each tissue type. It should be noted that the distance between the tissue types was always greater than the distance between the normal-tumor pairs. In addition, principal component analysis (PCA), demonstrated the disparity in the OGFGT expression profiles between the normal and tumor pairs across the different cancer types studied.

The relative importance of the classifying features using the area under the receiver operating characteristic (ROC) curve (AUROC) in identifying the cancer type and the normal-tumor label showed that some OGFGTs were of relatively high importance in all cancer types while the importance of other O-glycan GTs were cancer-type-specific. For example, FUT5, B3GNT7, ST3GAL1, FUT11, GALNT3, B4GALT3, and others were of high importance across all types of tested solid tumors while B4GALT3, FUT5, FUT11, ST3GAL1 and others were of particular importance in discriminating between cancer and non-cancer samples in kidney (or liver or lung).

Overall, the model classifier, based on the expression profiles of 55 GT genes, was able to distinguish cancer from normal samples in several types of solid tumors highlighting the ability of GT genes to act as biomarkers for carcinogenesis.

Alterations in O-Glycan Glycosyltransferase Expression Profiles are Cancer-Type-Specific Since O-glycan GT alterations in expression levels were associated with neoplasia, the present studies investigated whether similar alterations in OGFGTs take place in different cancer types or whether OGFGTs alter their expression levels in a cancer-type-specific manner OGFGTs expression profiles across a wide array of 23 cancer types from the TCGA dataset was compared (FIG. 3). Unsupervised hierarchical clustering of 11015 samples was performed and it revealed that the OGFGT genes exhibited distinct expression profiles across the different cancer types. Further, a cross correlation network based on LDA projections showed that these OGFGT expression profiles could separate a population of cancer samples into their respective distinct types. The constructed network can be further used to reveal the relative distance between cancer types implying potentially similar phenotypes, behaviors or clinical responses among correlated cancer types. Therefore using this pipeline (FIG. 1A), a model classifier using these OGFGT genes was developed. The predictive model was validated on an internal testing subset (FIG. 3A). The model achieved cross validation accuracy of 93.95% and 93.56% on the testing subset and its performance on the internal testing was acceptably high on most of the cancer types (FIG. 3A).

To confirm that the performance of this cancer-type classifier was reproducible (i.e. the model predictions are not over- or under-fitted), the OGFGT predictive model to classify cancer samples obtained from the Genotype-Tissue Expression (GTEx) project (PMID: 23715323) was used. TCGA and GTEx data as normalized by Wang et al., (PMID: 29664468) who developed a pipeline to unify cancer normal and tumor RNA sequencing data to account for study-specific biases, was used (see methods for details). The normalized TCGA dataset was then used to develop a cancer type RDA predictive model based on the expression data of the OGFGT from the TCGA (n=5564) spanning 10 cancer types. The 10-fold cross-validation accuracy of the predictive model was 96.79%. The model was then tested on the normalized GTEx dataset as an external dataset (FIG. 3B) with an overall accuracy of 91% (FIG. 3B). Validation of the model on an external dataset showed that O-glycan type GTs can reliably classify cancer samples into distinct cancer types.

Overall, these findings show that alterations in OGFGT expression levels are cancer-type specific. Furthermore, the accuracy of predicting a specific cancer type depends on high dimensional combinations of OGFGT genes, and not simply on single OGFGT genes, in order to identify cancer-type-specific expression signatures. It is believed that this is the first study to show that this curated set of O-glycan GT genes can predict both cancer state (i.e. cancer or normal) and type.

O-Glycan Glycosyltransferase Expression Signatures Predict Cancer Subtypes

Glioblastoma multiforme (GBM) is one of the most invasive and aggressive brain tumors and thus novel diagnostic and prognostic markers are urgently needed. Although ample studies have characterized clinically relevant subtypes of glioblastoma,[16,17] classifying glioblastoma subtypes according to the mutation status of isocitrate dehydrogenase (IDH) is one of the most widely used systems for GBM classification.[18-21] Several glycosyltransferases were shown to exhibit different patterns among GBM subtypes.[22-31] However, a global view of the alterations of O-glycan GTs in glioblastoma, in particular, has not previously been explored. Therefore, the ability of the OGFGT genes to classify cancer subtypes in GBM was investigated. The studies also examined use of the OGFGT-based model as a prognostic and/or diagnostic marker to predict glioblastoma IDH subtypes. The TCGA dataset included three distinct subtypes of GBM according to IDH mutation status: IDH wild type (IDHwt; n=242), IDH mutant with 1p/19q co-deletion (IDHmut-code1; n=168) and IDH mutant without 1p/19q co-deletion (IDHmut-non-code1; n=248).

OGFGTs were able to separate the glioblastoma samples into two major groups in line with their clinical annotation (IDHwt and IDHmut). The IDHmut cluster could be classified further into 3 clusters: two corresponding to IDHmut-non-code1 while the third corresponding to IDHmut-code1. Using hierarchical clustering, the OGFGT genes clustered the samples into 4 clusters (G1-4) depending on OGFGT expression. For example, IDHwt samples were low in gene cluster one but high in cluster two while, in contrast, IDHmut samples were high in gene cluster one and low in cluster two. Moreover, IDHmut-code1 could be discerned from IDHmut-non-code1 by genes in clusters two and four. Moreover, multi-dimensional scaling (MDS) using PCA and LDA analyses illustrated that the OGFGT genes were able to cluster the glioblastoma samples into their respective clinical subtypes.

The average normalized expression of the three glioblastoma subtypes was also explored and showed opposite trends between the IDHwt and IDHmut subtypes. Strikingly, IDHwt gravitated towards low expression of a number of fucosyltransferase (FUT) genes such as FUT9, FUT3, FUT6, FUT5, FUT2, and FUT1. Moreover, although the IDHmut-code1 and the IDHmut-non-code1 subtypes have the same general trend regarding OGFGT gene expression, they can be differentiated by a number of genes including FUT5, GCNT2, B4GALT2, ST3GAL3, FUT4 and B3GNT5.

Figure 6A:
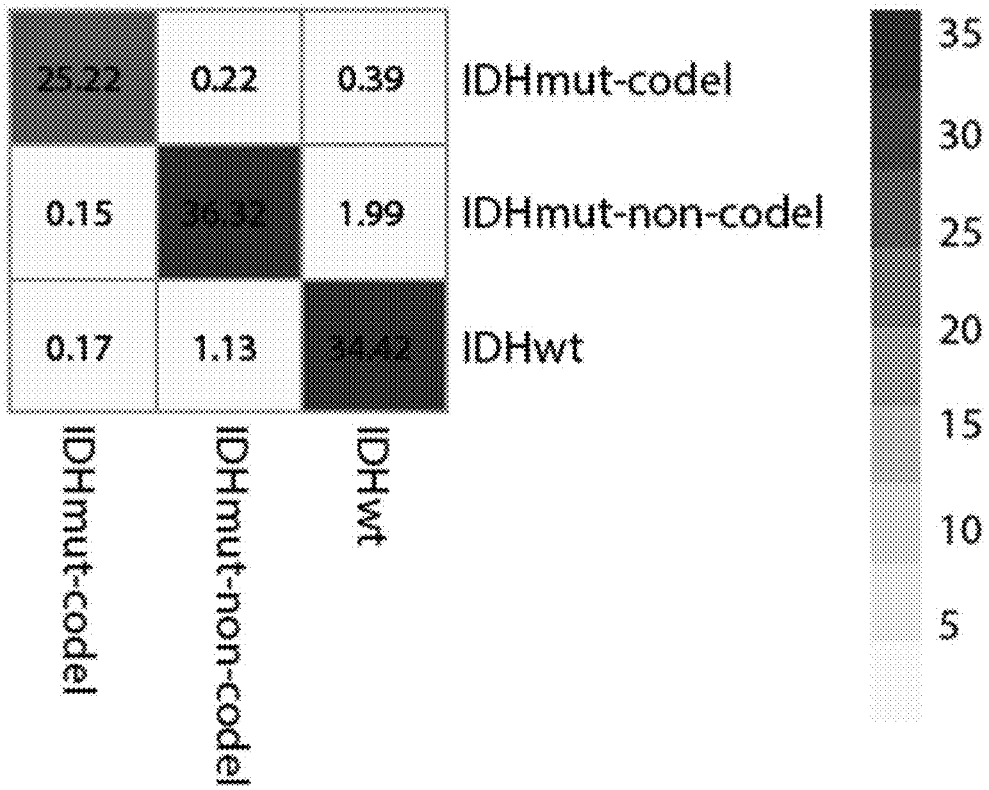
Figure 6B:
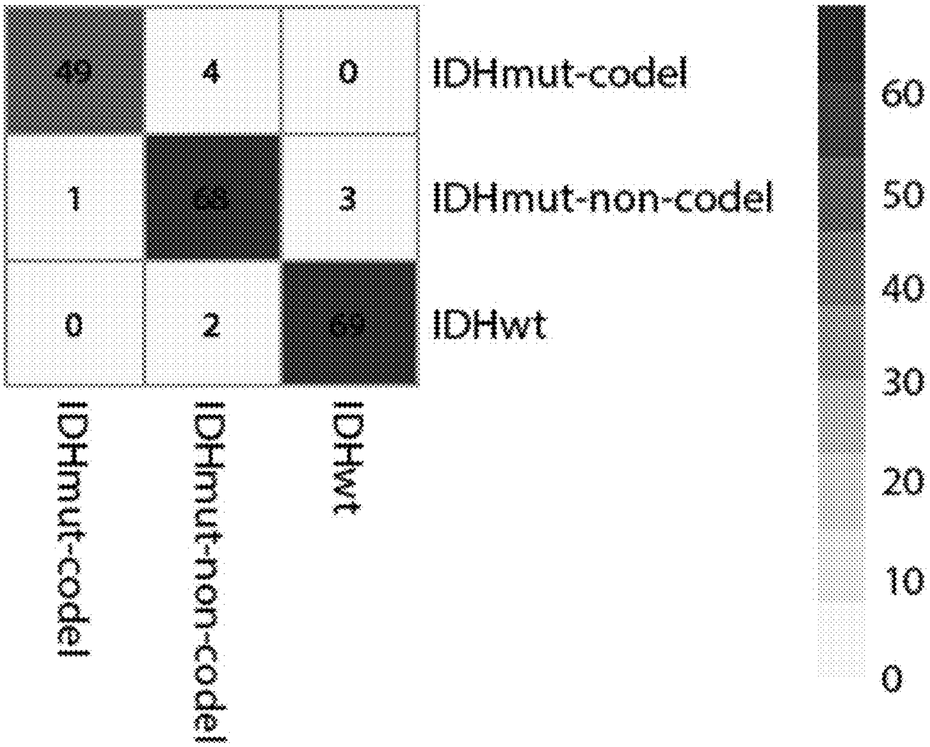

Cross validation showed that the RDA glioblastoma subtype predictive model is 95.95% accurate; FIG. 6A, 6C). The model showed highly promising performance metrics (FIG. 6A, 6C). The prediction of the glioblastoma subtype on the samples of the testing dataset was 94.90% accurate with rigorous prediction of class labels and exclusion of non-labels (FIG. 6B, 6D).

Subsequently, the relative importance of the OGFGT genes to identify the glioblastoma subtype using the model-independent ROC method was examined. Interestingly, the genes that ranked high in the feature importance analysis spanned different enzyme families. The genes identified can be used as glioblastoma bio-markers when used in combination (model-based prediction).

Figure 5A:
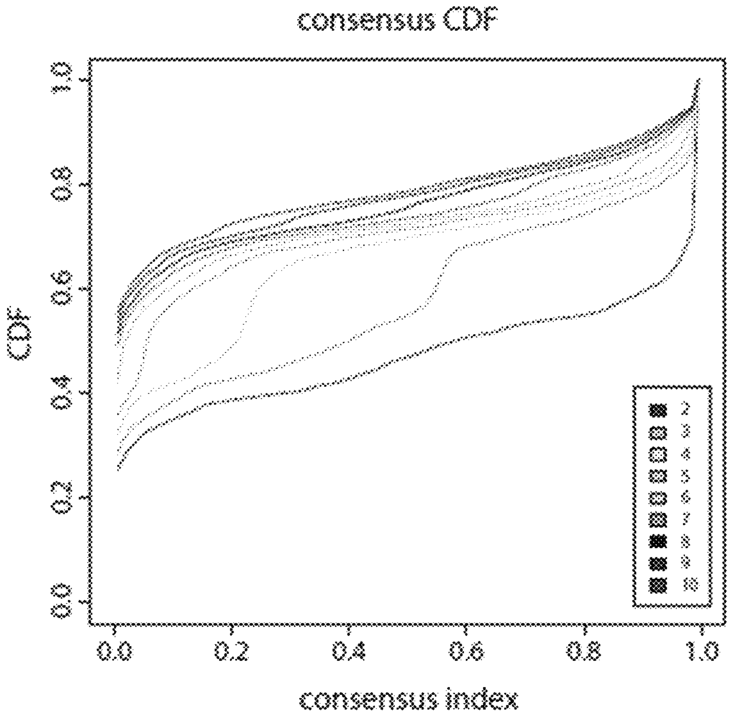
FIG. 5A. Consensus clustering of the glioblastoma samples using OGFGT genes expression. Glioblastoma samples from the TCGA dataset (n=658) were used for de novo clustering based on the expression of the OGFGT genes by scanning the k values from 2 to 10. CDF curve accumulate consensus score from samples with low consensus scores (rarely cluster together across different clustering iterations) to samples with high consensus scores. Bumps in the CDF curve indicate assignment ambiguity.
Figure 5B:
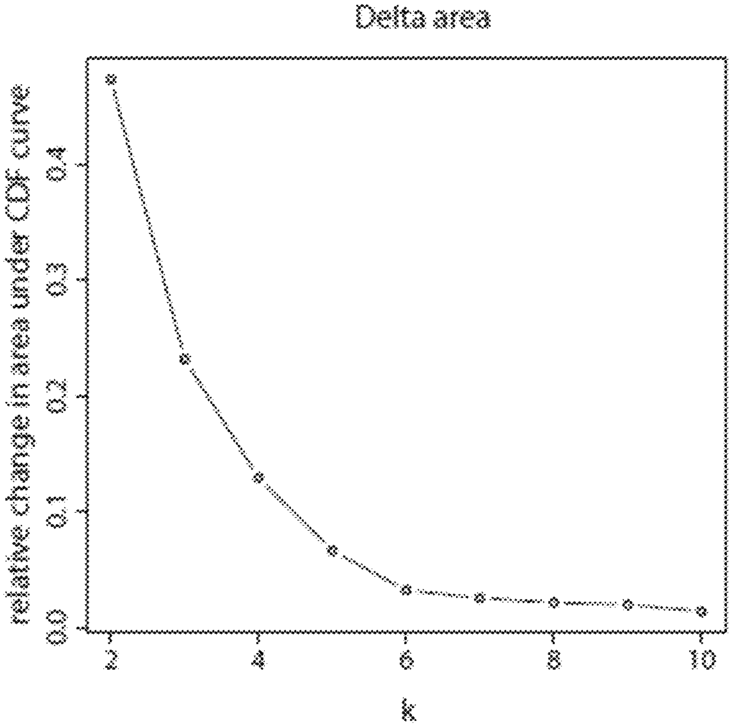
FIG. 5B. The relative change in the area under the CDF curve across different k values from 2 to 10. The optimal value of k has the least increase in the area under the curve (AUC) from k to k+1. The optimal solution showed the least detectable amount of ambiguity in the consensus matrix and the CDF curve.
Figure 5C:
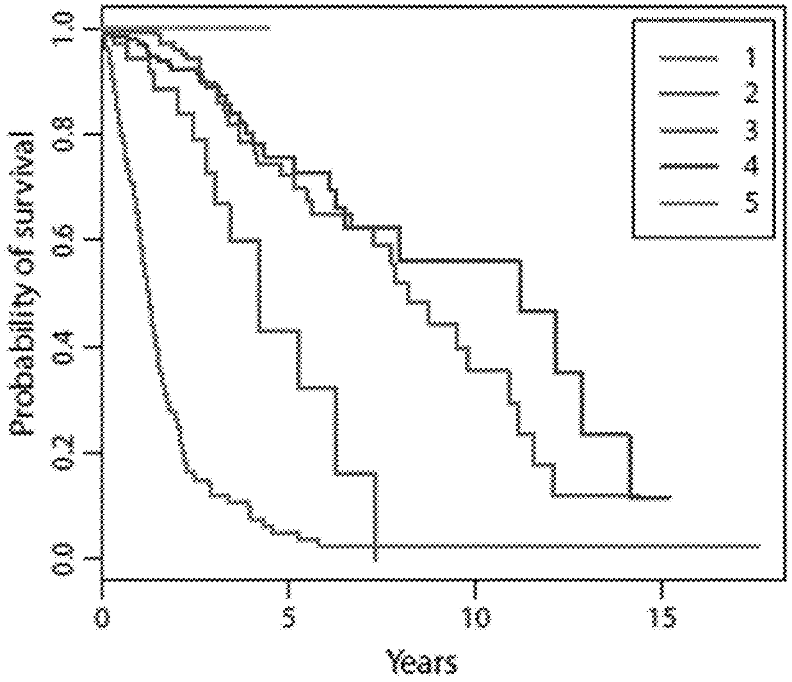
FIGS. 5C-D. Survival profiles of the de novo clusters of the glioblastoma samples from the TCGA dataset using the expression data of the OGFGT genes.
Figure 5D:
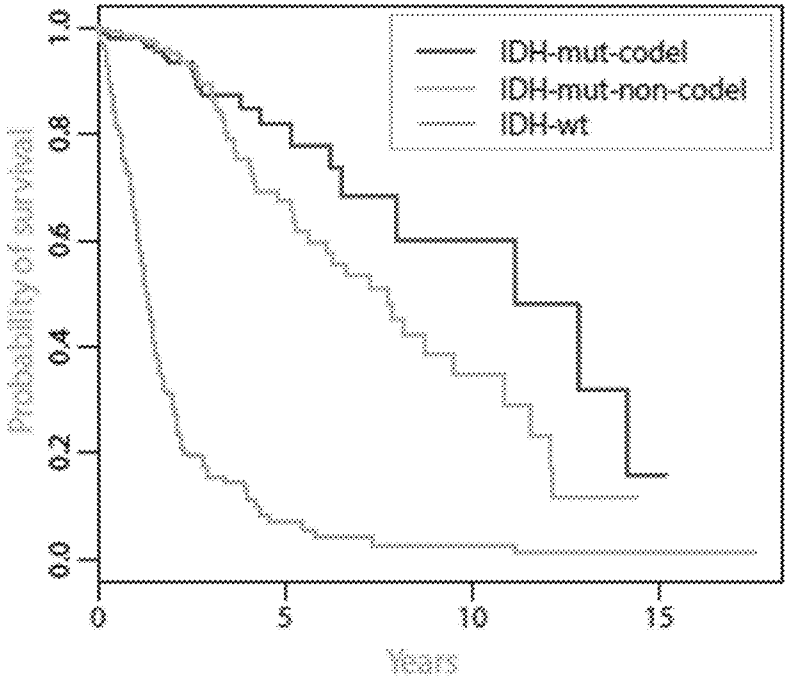

O-Glycan Glycosyltransferases Expression Signature Predicts Patient Survival in Glioblastoma Multiforme To examine the prognostic value of OGFGT expression signatures in GBM, the ability of OGFGT to cluster the glioblastoma samples into de novo clusters with significantly distinct survival profiles was investigated. Shrunken centroid consensus clustering was carried out using the normalized expression data of the OGFGT genes from the TCGA dataset (n=658) over $10^4$ subsampling iterations. Following assessment of the consensus matrix, the cumulative distribution function (CDF) curve (FIG. 5A) and the relative change in the area under the CDF curve (FIG. 5B), the data showed that k=5 is the optimal solution; this suggests that GBM samples can be reliably grouped into 5 distinct subtypes that are significantly different in their survival profiles (FIG. 5C-E). Our analysis also showed the highest value of k with least change in the area under the CDF curve. Interestingly, cluster one had a survival profile that is almost equal to the survival profile of the IDHwt subtype group (FIG. 5C-E). Also, cluster three and four had survival profiles close to the survival profiles of IDHmut-non-code1 and IDHmut-code1 respectively (FIG. 5C-E). Noticeably, the OGFGT-based consensus clustering exposed a novel risk group (cluster two) that indicated significantly less survival probability than cluster three and four. This previously unidentified risk group corresponded to the IDHmut-non-code1 and IDHmut-code1 GBM subtypes (FIG. 5C-E). Moreover, a small group with significantly high survival probability was identified (cluster five, FIG.

5C-E) where the OGFGT-based groups showed a significant association between the likelihood of survival and the class assignment (p=0).

Discussion

The studies described above were based on the hypothesis that the expression signature of a group of GTs, specifically the O-glycan type GTs, in cancer cells have the power to predict and discriminate cancerous cells, cancer types and subtypes. Indeed, the data shows that a global view of the expression profile of OGFGTs in cancer cells has the power to discriminate cancer samples from their normal counterparts highlighting their potential use as diagnostic markers for cancer. The OGFGT genes were also able to distinguish between up to 23 types of solid tumors and even predicted distinct subtypes within the same type of cancer, e.g. GBM. As a proof of concept for the potential use of OGFGTs as prognostic markers, the data in this application shows that OGFGT genes can predict the survival profiles of the different subtypes of GBM.

Although the expression of GTs in various cancer types has been studied,[3,44-47] the present study is the first to propose and demonstrate the use of OGFGT expression signatures, in particular, for predicting cancer types. A recent study outlined the differential expression of 210 GTs in six types of cancer using microarray data and found that each cancer type presented a distinct signature of GT expression that had enough power to develop a cancer classifier with about 70% accuracy of cancer type prediction in the external validation task.[11] In contrast, the current study shows the ability of a curated set of 55 GT genes of the O-glycan biosynthesis pathway to distinguish between as many as 23 (versus 6)[11] types of cancer. Additionally, the disclosed OGFGT predictor model for cancer-type outperformed the reported classifier with about 91% accuracy of prediction in an external validation task given a higher number of cancer types.

Thus, the current model which was developed using a curated set of 55 OGT genes outperformed previous models that have attempted to classify cancer types with 200+ GT genes[11] (PMID: 27198045).

The complexity of the problem sheds light on the power of our approach. Studying the expression profiles of the OGFGTs in high dimensional space enriches the ability to discriminate between cancer types and makes use of what is usually considered an insignificant difference in expression in a single dimension (thus, promoting the use of a limited group of genes as bio-markers rather than single genes). Further, the complex correlations between the expression signatures of the OGFGTs and the cancer class reflect a deeper understanding of the development of cancer, the evolution of its subpopulations and, consequently, the behavior of the diverse groups of cancers during crucial programs such neoplastic transformation, metastatic migration and EMT-OGFGT expression signatures of cancer heterogeneity and transformation.

A few reports studied the expression of sialyltransferases (STs) and fucosyltransferases (FUTs) in glioblastoma irrespective of the IDH mutation status. It has been reported that α2,3-STs, but not α2,6-STs, were up-regulated in glioblastoma.[48,49] The present studies show that the more aggressive IDHwt up-regulated α2,3-STs such as ST3GAL1, ST3GAL2 and ST3GAL4 while, on the other hand, the less invasive IDHmut samples up-regulated α2,6-STs such as ST6GALNAC1. Likewise, stage-specific embryonic antigen (SSEA-1) is up-regulated in tumor-initiating cells (TICs) in glioblastoma.[30] SSEA-1 is non-sialylated Lewis X ($Le^x$) usually synthesized by the action of α1,3FUTs. Nevertheless, no clear link between TICs and IDH status has been established in GBM. The studies here reveal that IDHwt up-regulated FUT4 while IDHmut up-regulated FUT9, FUT3, FUT6, FUT5, FUT2 and FUT1. Interestingly, FUT3, 4, 5, 6 and 9 can synthesize $Le^x$ structures but FUT9 is more efficient than the others and is able to fucosylate the remote internal N-acetyllactosamine units of α2,3-sialylated polylactosamine structures.[51,52]

It has been reported that glycosylation is involved in the modulation of a number of crucial signaling proteins in GBM. However, the role of glycosylation in modulating cell-cell adhesion, cell-matrix adhesion, and subsequently, local invasiveness and distant migration remains elusive. Separately, the value of the OGFGT genes in differentiating between the glioblastoma subtypes was investigated. The present studies show that the OGFGTs genes can cluster the glioblastoma subtypes using unsupervised techniques including hierarchical clustering and PCA, and classify them using the supervised techniques such as LDA and RDA-based predictive modeling. De novo clustering using the expression of OGFGT genes brought the glioblastoma samples together into groups that are significantly associated with the likelihood of survival. Furthermore, OGFGTs were able to identify two novel classes of glioblastoma that showed significantly distinct survival profiles other than those already known for the glioblastoma subtypes.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

REFERENCES

1 Varki, et al. *Glycobiology* 27, 3-49, doi:10.1093/glycob/cww086 (2017).
2 Varki, A., Kannagi, R., Toole, B. & Stanley, P. in *Essentials of Glycobiology* (eds rd et al.) 597-609 (2015).
3 Pinho, et al. *Nat Rev Cancer* 15, 540-555, doi:10.1038/nrc3982 (2015).
4 Munkley, et al *Oncotarget* 7, 35478-35489, doi:10.18632/oncotarget.8155 (2016).
5 Hebbar, et al. *Int J Biol Markers* 18, 116-122 (2003).
6 Dall'Olio, et al. *Int J Mol Sci* 18, doi:10.3390/ijms18050998 (2017).
7 Oliveira-Ferrer, et al. *Semin Cancer Biol* 44, 141-152, doi:10.1016/j.semcancer.2017.03.002 (2017).
8 Meany, et al *Clin Proteomics* 8, 7, doi:10.1186/1559-0275-8-7 (2011).
9 Rini, J. M. & Esko, J. D. in *Essentials of Glycobiology* (eds rd et al.) 65-75 (2015).
10 Liu, X. et al. *PLoS One* 8, e72704, doi:10.1371/journal-.pone.0072704 (2013).
11 Ashkani, et al. *Sci Rep* 6, 26451, doi:10.1038/srep26451 (2016).
12 Kudelka, et al. *Adv Cancer Res* 126, 53-135, doi:10.1016/bs.acr.2014.11.002 (2015).
13 Burchell, et al. *Biochem Soc Trans* 46, 779-788, doi:10.1042/BST20170483 (2018).

14 Brockhausen, et al *EMBO Rep* 7, 599-604, doi:10.1038/sj.embor.7400705 (2006).
15 Wang, Q. et al. *bioRxiv,* 110734, doi:10.1101/110734 (2017).
16 Verhaak et al. *Cancer Cell* 17, 98-110, doi:10.1016/j.ccr.2009.12.020 (2010).
17 Marziali, G. et al. Metabolic/Proteomic Signature Defines Two Glioblastoma Subtypes With Different Clinical Outcome. *Sci Rep* 6, 21557, doi:10.1038/srep21557 (2016).
18 Kebir, S. et al. *Clin Nucl Med*, doi:10.1097/RLU.0000000000002398 (2018).
19 Miller, et al *Cancer* 123, 4535-4546, doi:10.1002/cncr.31039 (2017).
20 Waitkus, M. S., Diplas, B. H. & Yan, H. Biological Role and Therapeutic Potential of IDH Mutations in Cancer. *Cancer Cell* 34, 186-195, doi:10.1016/j.ccell.2018.04.011 (2018).
21 Wesseling, P. & Capper, D. WHO 2016 Classification of gliomas. *Neuropathol Appl Neurobiol* 44, 139-150, doi:10.1111/nan.12432 (2018).
22 Shoreibah, et al. *J Biol Chem* 268, 15381-15385 (1993).
23 Yamamoto, H. et al. Beta1,6-N-acetylglucosamine-bearing N-glycans in human gliomas: implications for a role in regulating invasivity. *Cancer Res* 60, 134-142 (2000).
24 Padhiar, et al. *Am J Cancer Res* 5, 1101-1116 (2015).
25 Nagae, et al. *Nat Commun* 9, 3380, doi:10.1038/s41467-018-05931-w (2018).
26 Hassani, et al., *Mol Cancer Res* 15, 1376-1387, doi:10.1158/1541-7786.MCR-17-0120 (2017).
27 Chong, et al., *J Natl Cancer Inst* 108, doi:10.1093/jnci/djv326 (2016).
28 Veillon, et al. *ACS Chem Neurosci* 9, 51-72, doi:10.1021/acschemneuro.7b00271 (2018).
29 Amoureux, et al. *BMC Cancer* 10, 91, doi:10.1186/1471-2407-10-91 (2010).
30 Son, et al., *Cell Stem Cell* 4, 440-452 (2009).
31 Cheray, et al. *Cancer Lett* 312, 24-32, doi:10.1016/j.canlet.2011.07.027 (2011).
32 Taniguchi, et al. *Adv Cancer Res* 126, 11-51 (2015).
33 Potapenko, et al. *Mol Oncol* 4, 98-118 (2010).
34 Magalhaes, et al. *Cancer Cell* 31, 733-735, (2017).
35 Tsuiji, et al. *Glycobiology* 13, 521-527, (2003).
36 Mungul, et al. *Int J Oncol* 25, 937-943 (2004).
37 Bresalier, et al. *Gastroenterology* 110, 1354-1367 (1996).
38 Julien, et al. *Breast Cancer Res Treat* 90, 77-84 (2005).
39 Kojima, et al. *Biochem Biophys Res Commun* 182, 1288-1295 (1992).
40 Petretti, et al. *Gut* 46, 359-366 (2000).
41 Ito, H. et al. *Int J Cancer* 71, 556-564 (1997).
42 Hanski, et al. *Glycoconj J* 13, 727-733 (1996).
43 Nakamori, et al. *Cancer Res* 53, 3632-3637 (1993).
44 Stowell, et al., *Annu Rev Pathol* 10, 473-510 (2015).
45 Drake, et al., *Adv Cancer Res* 126, 345-382 (2015).
46 Holst, et al., *Adv Cancer Res* 126, 203-256 (2015).
47 Lemjabbar-Alaoui, et al., *Adv Cancer Res* 126, 305-344 (2015).
48 Yamamoto, et al. *J Neurochem* 68, 2566-2576 (1997).
49 Kaneko, et al. *Acta Neuropathol* 91, 284-292 (1996).
50 Yamamoto, H., Oviedo, A., Sweeley, C., Saito, T. & Moskal, J. R. Alpha2,6-sialylation of cell-surface N-glycans inhibits glioma formation in vivo. *Cancer Res* 61, 6822-6829 (2001).
51 Nishihara, et al. *FEBS Lett* 462, 289-294 (1999).
52 Toivonen, et al., *Glycobiology* 12, 361-368 (2002).
53 Yeo, I.-K. & Johnson, R. A. A New Family of Power Transformations to Improve Normality or Symmetry. *Biometrika* 87, 954-959 (2000).
54 Wang Q., et al., Sci Data. 5:180061 (2018).

We claim:

1. A method for treating liver, kidney, breast, lung, or brain cancer in a human subject, wherein the human subject is identified as having liver, kidney, breast, lung, or brain cancer by a method comprising (a) determining the mRNA expression levels of 55 O-glycan-forming glycosyltransferases (OGFGTs) in a tumor sample from the human subject, wherein the tumor sample comprises liver, kidney, breast, lung, or brain cells and/or tissue, and wherein the 55 OGFGTs are: ST3GAL3, B3GNT3, C1GALT1C1, B3GNT6, CHST1, B4GALT5, B4GALT1, GALNT8, B4GALT3, GCNT7, B3GNT7, B4GALT2, FUT5, FUT4, GALNT4, ST3GAL1, ST3GAL2, FUT11, FUT2, FUT7, GALNT3, B3GNT2, GCNT2, FUT1, B4GALT4, FUT3, B3GNT5, CHST2, GALNT2, FUT9, GCNT4, B3GNT8, GALNT13, GALNT7, GALNT10, B3GNT9, GALNT6, C1GALT1, GALNT12, FUT10, B3GNT4, FUT6, B3GNT1, CHST4, ST3GAL4, GALNT5, ST3GAL6, GALNT1, GALNT9, GCNT1, GALNT14, GALNT11, ST6GALNAC1, GCNT3, and ST6GAL1;

(b) analyzing the mRNA expression levels of the 55 OGFGTs determined in (a) with a classifier that can distinguish between cancer and non-cancer samples by comparing the mRNA expression level of each OGFGT in the tumor sample to a reference level;

(c) identifying the human subject as having liver cancer, kidney cancer, breast cancer, lung cancer, or brain cancer; and (d) administering an anticancer treatment to the human subject identified as having liver cancer, kidney cancer, breast cancer, lung cancer, or brain cancer, wherein the anticancer treatment is selected from the group consisting of surgery, chemotherapy, radiation therapy, immunotherapy, gene therapy, and combinations thereof, and wherein the reference levels are: (a) the expression levels in a non-cancerous sample from the subject or the expression levels in a non-cancerous sample from one or more different subjects, wherein the non-cancerous sample is of the same tissue type as the sample from the subject; or (b) the expression levels in a cancerous sample from one or more different subjects, optionally wherein the cancerous sample is of the same tissue type as the sample from the subject.

2. The method of claim 1, wherein the OGFGT expression levels in the sample is detected as the same, below, or above the reference levels.

3. The method of claim 1, wherein the reference levels are the expression levels in a non-cancerous sample from the subject or the expression levels in a non-cancerous sample from one or more different subjects.

4. The method of claim 1, wherein the reference levels are the expression levels in a cancerous sample from one or more different subjects, optionally wherein the cancerous sample is of the same tissue type as the sample from the subject.

5. The method of claim 1, wherein analysis of mRNA expression comprises RNA-sequencing.

6. The method of 1, wherein the cancer is brain cancer.

7. The method of claim 6, wherein the brain cancer is Glioblastoma multiforme (GBM).

8. The method of claim 7, wherein the subject is diagnosed as having a subtype of Glioblastoma multiforme (GBM) selected from the group consisting of IDH wild type GBM, IDH mutant with 1p/19q co-deletion GBM, or IDH mutant without 1p/19q co-deletion GBM.

9. The method of claim 8, wherein the subject is determined to have (a) lower expression levels of the OGFGTs selected from the list consisting of B3GNT3, ST3GAL4, GALNT6, ST3GAL1, B3GNT2, GCNT1, CHST4, GALNT12, GALNT5, C1GALT1C1, B3GNT8, CHST2, B3GNT7, GALNT3, B3GNT9, B4GALT4, C1GALT1, GALNT7, FUT4, B4GALT1, GALNT2, B3GNT5, and GALNT4; and/or (b) higher expression levels of the OGFGTs selected from the list consisting of GALNT14, GALNT9, ST6GALNAC1, B3GNT1, CHST1, GALNT13, FUT9, FUT3, FUT6, and FUT5 compared to the reference levels; and wherein the subject is diagnosed as having the IDH wild type subtype of GBM.

10. The method of claim 8, wherein the subject is determined to have (a) higher expression levels of the OGFGTs selected from the list consisting of B3GNT3, ST3GAL4, GALNT6, ST3GAL1, B3GNT2, GCNT1, CHST4, GALNT12, GALNT5, C1GALT1C1, B3GNT8, CHST2, B3GNT7, GALNT3, B3GNT9, B4GALT4, C1GALT1, GALNT7, FUT4, B4GALT1, GALNT2, B3GNT5, and GALNT4; and/or (b) lower expression levels of the OGFGTs selected from the list consisting of GALNT14, GALNT9, ST6GALNAC1, B3GNT1, CHST1, GALNT13, FUT9, FUT3, FUT6, and FUT5 compared to the reference levels; and wherein the subject is diagnosed as having an IDH mutant subtype of GBM.

11. The method of claim 8, wherein the subject is diagnosed as having a IDH mutant with 1p/19q co-deletion GBM or IDH mutant without 1p/19q co-deletion GBM based on the expression levels of the OGFGTs comprising FUT5, GCNT2, B4GALT2, ST3GAL3, FUT4, and, B3GNT5.

12. The method of claim 1, wherein the subject undergoes one or more additional diagnostic assay(s) selected from blood tests, mammography, non-invasive imaging, tissue biopsy, HER2 testing, hormone status testing, and combinations thereof.

13. The method of claim 1, wherein chemotherapy comprises administration to the subject of an effective amount of a chemotherapeutic agent selected from the group comprising Azacitidine, Capecitabine, Carmofur, Cladribine, Clofarabine, Cytarabine, Decitabine, Floxuridine, Fludarabine, Fluorouracil, Gemcitabine, Mercaptopurine, Nelarabine, Pentostatin, Tegafur, Methotrexate, Daunorubicin, Doxorubicin, Epirubicin, Docetaxel, Paclitaxel, Vinblastine, Vincristine, and Cisplatin.

* * * * *